(12) United States Patent
Suh et al.

(10) Patent No.: US 12,370,155 B2
(45) Date of Patent: *Jul. 29, 2025

(54) ANTICANCER COMPOSITION

(71) Applicant: NOAHM INC., Incheon (KR)

(72) Inventors: Man-Chul Suh, Incheon (KR); Yieun Jung, Gyeonggi-do (KR); Eun Ji Kim, Gangwon-do (KR); Jae In Jung, Gangwon-do (KR)

(73) Assignee: NOAHM INC., Incheon (KR)

( * ) Notice: Subject to any disclaimer, the term of this patent is extended or adjusted under 35 U.S.C. 154(b) by 734 days.

This patent is subject to a terminal disclaimer.

(21) Appl. No.: 17/293,390

(22) PCT Filed: Nov. 11, 2019

(86) PCT No.: PCT/KR2019/015251
§ 371 (c)(1),
(2) Date: May 12, 2021

(87) PCT Pub. No.: WO2020/101302
PCT Pub. Date: May 22, 2020

(65) Prior Publication Data
US 2022/0000810 A1 Jan. 6, 2022

(30) Foreign Application Priority Data
Nov. 12, 2018 (KR) .................. 10-2018-0138345

(51) Int. Cl.
| | | |
|---|---|---|
| A23L 33/125 | (2016.01) | |
| A23L 33/00 | (2016.01) | |
| A61K 31/05 | (2006.01) | |
| A61K 31/155 | (2006.01) | |
| A61K 31/6615 | (2006.01) | |
| A61K 31/7004 | (2006.01) | |
| A61P 35/00 | (2006.01) | |

(52) U.S. Cl.
CPC .......... A61K 31/155 (2013.01); A23L 33/125 (2016.08); A23L 33/40 (2016.08); A61K 31/05 (2013.01); A61K 31/6615 (2013.01); A61K 31/7004 (2013.01); A61P 35/00 (2018.01); *A23V 2002/00* (2013.01)

(58) Field of Classification Search
CPC .. A61K 31/155; A61K 31/05; A61K 31/6615; A61K 31/7004; A61K 31/683; A61K 2300/00; A23L 33/125; A23L 33/40; A61P 35/00; A23V 2002/00
See application file for complete search history.

(56) References Cited

U.S. PATENT DOCUMENTS

2014/0235558 A1 8/2014 Kim et al.
2022/0081482 A1 3/2022 Suh et al.

FOREIGN PATENT DOCUMENTS

| KR | 10-2011-0136753 A | 12/2011 |
|---|---|---|
| KR | 10-2013-0015669 A | 2/2013 |
| KR | 10-2014-0026981 A | 3/2014 |
| KR | 10-2016-0109926 A | 9/2016 |
| KR | 10-2017-0083997 A | 7/2017 |
| KR | 10-2017-0103732 A | 9/2017 |
| WO | WO-2016/140714 A1 | 9/2016 |
| WO | WO-2017/130126 A1 | 8/2017 |

OTHER PUBLICATIONS

Andrzejewski, S., Siegel, P. M., & St-Pierre, J. Metabolic Profiles Associated With Metformin Efficacy in Cancer. Frontiers in Endocrinology, 9. https://doi.org/10.3389/fendo.2018.00372 (Year: 2018).*
Sahra et al. Targeting Cancer Cell Metabolism: The Combination of Metformin and 2-Deoxyglucose Induces p53-Dependent Apoptosis in Prostate Cancer Cells. Cancer Research, 70(6), 2465-2475. https://doi.org/10.1158/0008-5472.can-09-2782 (Year: 2010).*
Lauretta, R., Lanzolla, G., Vici, P., Mariani, L., Moretti, C., & Appetecchia, M. Insulin-Sensitizers, Polycystic Ovary Syndrome and Gynaecological Cancer Risk. International Journal of Endocrinology, 2016, 1-17. https://doi.org/10.1155/2016/8671762 (Year: 2016 ).*
Nas, K., & Tűű, L. A comparative study between myo-inositol and metformin in the treatment of insulin-resistant women. European Review for Medical and Pharmacological Sciences, 21, 77-82. https://www.europeanreview.org/article/13000 (Year: 2017).*
Nattrass, M., Todd, P. G., Hinks, L., Lloyd, B., & Alberti, K. G. M. M. Comparative effects of phenformin, metformin and glibenclamide on metabolic rhythms in maturity-onset diabetics. Diabetologia, 13(2), 145-152. https://doi.org/10.1007/bf00745143 (Year: 1977).*
Vucenik, I., & Shamsuddin, A. M. Cancer inhibition by inositol hexaphosphate (IP6) and inositol: from laboratory to clinic. The Journal of Nutrition, 133(11 Suppl 1), 3778S3784S. https://doi.org/10.1093/jn/133.11.3778S (Year: 2003).*
Apotex NA LTD. Metformin. New Zealand Data Sheet. (Year: 2018).*

(Continued)

*Primary Examiner* — Yih-Horng Shiao
*Assistant Examiner* — Hoi Yan Nmn Lee
(74) *Attorney, Agent, or Firm* — MARSHALL, GERSTEIN & BORUN LLP

(57) ABSTRACT

The present invention relates to a composition comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof. The composition according to the present invention exhibits a synergistic anticancer effect by appropriately combining specific drugs having a problem that needs to be used in a large amount, thereby making it possible to kill cancer cells in a small amount and effectively treat the cancer. Furthermore, the composition of the present invention may kill only cancer cells without side effects by exhibiting a specific toxic effect on cancer cells without showing toxicity on normal cells and thus be usefully used as an anticancer agent and for preventing or improving cancer.

5 Claims, 12 Drawing Sheets

(56) References Cited

OTHER PUBLICATIONS

Hada et al. D-chiro-Inositol and Pinitol Extend the Life Span of Drosophila melanogaster. The Journals of Gerontology Series A: Biological Sciences and Medical Sciences, 68(3), 226-234. https://doi.org/10.1093/gerona/gls156 (Year: 2012).*
Bizjak, M., Malavašič, P., Dolinar, K., Pohar, J., Sergej Pirkmajer, & Pavlin, M. Combined treatment with Metformin and 2-deoxy glucose induces detachment of viable MDA-MB-231 breast cancer cells in vitro. Nature, 7(1). https://doi.org/10.1038/s41598-017-01801-5 (Year: 2017).*
Examination Report from Australian Patent Application No. 2019381050 dated May 13, 2022.
Andrzejewski et al., "Metformin directly acts on mitochondria to alter cellular bioenergetics," Cancer & Metabolism 2:12, 14 pages (2014).
Bizjak et al., "Combined treatment with Metformin and 2-deoxy glucose induces detachment of biable MDA-MB-231 breast cancer cells in vitro," Scientific Reports, 7:1761, 14 pages (2017).
Cheong et al., "Dual Inhibition of Tumor Energy Pathway by 2-Deoxyglucose and Metformin is Effective against a Broad Spectrum of Preclinical Cancer Models," Mol Cancer Ther 10(12):2350-2362 (2011).
Mokhtari et al., "Combination therapy in combating cancer," Oncotarget 8(23):38022-38043 (2017).
Raez et al., "A phase I dose-escalation trial of 2-deoxy-D-glucose alone or combined with docetaxel in patients with advanced solid tumors," Cancer Chemother Pharmacol 71:523-530 (2013).
Sahra et al., "Targeting Cancer Cell Metabolism: The Combination of Metformin and 2- Deoxyglucose Induces p53-Dependent Apoptosis in Prostate Cancer Cells," Cancer Res 70:2465- 2475 (2010).
Vucenik et al., "Cancer Inhibition by Inositol Hexaphosphate (IP6) and Inositol: From Laboratory to Clinic," International Research Conference on Food, Nutrition, and Cancer, Jul. 17-18, 2003.
Vucenik et al., "Protection Against Cancer by Dietary IP6 and Inositol," Nutrition and Cancer 55(2):109-125 (2006).
Wokoun et al., "Co-treatment of breast cancer cells with pharmacologic doses of 2-deoxy-D- glucose and metformin: Starving tumors," Oncology Reports 37:2418-2424 (2017).
Zhang et al., "2-Deoxy-D-glucose targeting of glucose metabolism in cancer cells as a potential therapy," Cancer Letters 355:176-183 (2014).
Bijnsdorp et al., "Analysis of Drug Interactions," Methods Mol Biol. 731:421-434 (2011).
Chou et al., "Theoretical Basis, Experimental Design, and Computerized Simulation of Synergism and Antagonism in Drug Combination Studies," Pharmacological Reviews, 58:621-681 (2006).
Pinto et al., "Combination Chemotherapy in Cancer: Principles, Evaluation and Drug Delivery Strategies," Current Cancer Treatment - Novel Beyond Conventional Approaches, www.intechopen.com, pp. 693-714 (2011).
Bacic et al., "Efficacy of $IP_6$ + inositol in the treatment of breast cancer patients receiving chemotherapy: prospective, randomized, pilot clinical study," Journal of Experimental & Clinical Cancer Research 29:12, 5 pages (2010).
Borghaei et al., "Nivolumab versus Docetaxel in Advanced Nonsquamous Non-Small-Cell Lung Cancer," N Engl J Med 373:1627-1639 (2015).
Buchbinder et al., "CTLA-4 and PD-1 Pathways Similarities, Differences, and Implications of Their Inhibition," American Journal of Clinical Oncology 39(1):98-106 (2016).
Couzin-Frankel, "Cancer Immunotherapy," Science 342:1432-1433 (2013).
Extended European Search Report for European Application No. 19907947.6, dated Nov. 14, 2022.
International Search Report and Written Opinion from International Application No. PCT/KR2019/018697 dated Apr. 7, 2020.
Kee et al., "Tumor bioenergetic: An emerging avenue for cancer metabolism targeted therapy," BMB Reports 47(3):158-166 (2014).
Kouidhi et al., "Targeting Tumor Metabolism: A New Challenge to Improve Immunotherapy," Frontiers in Immunology 9:11 pages (2018).
Office Action issued in Japanese Patent Application No. 2021-538354 dated Jul. 20, 2022.
Scharping et al., "Efficacy of PD-1 Blockade Is Potentiated by Metformin-Induced Reduction of Tumor Hypoxia," Cancer Immunol Res 5:9-16 (2017).
Schneider, "Inositol transport proteins," FEBS Lett, 589 (10):1049-58 (2015).
Xiao-Bin et al., "Combination of 2-deoxyd-glucose and metformin for synergistic inhibition of non-small cell lung cancer: A reactive oxygen species and P-p38 mediated mechanism", Biomedicine & Pharmacotherapy, vol. 84, pp. 1575-1584 (Nov. 2016).
Zheng et al., "Targeting metabolic vulnerabilities of MDSCs to enhance the anti-tumor activity of PD-1 blockade in melanoma", *Journal of Investigative Dermatology*, 137:5, Supplement 1, p. S137, Abstract No. 798, 2017.

* cited by examiner

[Fig. 1]
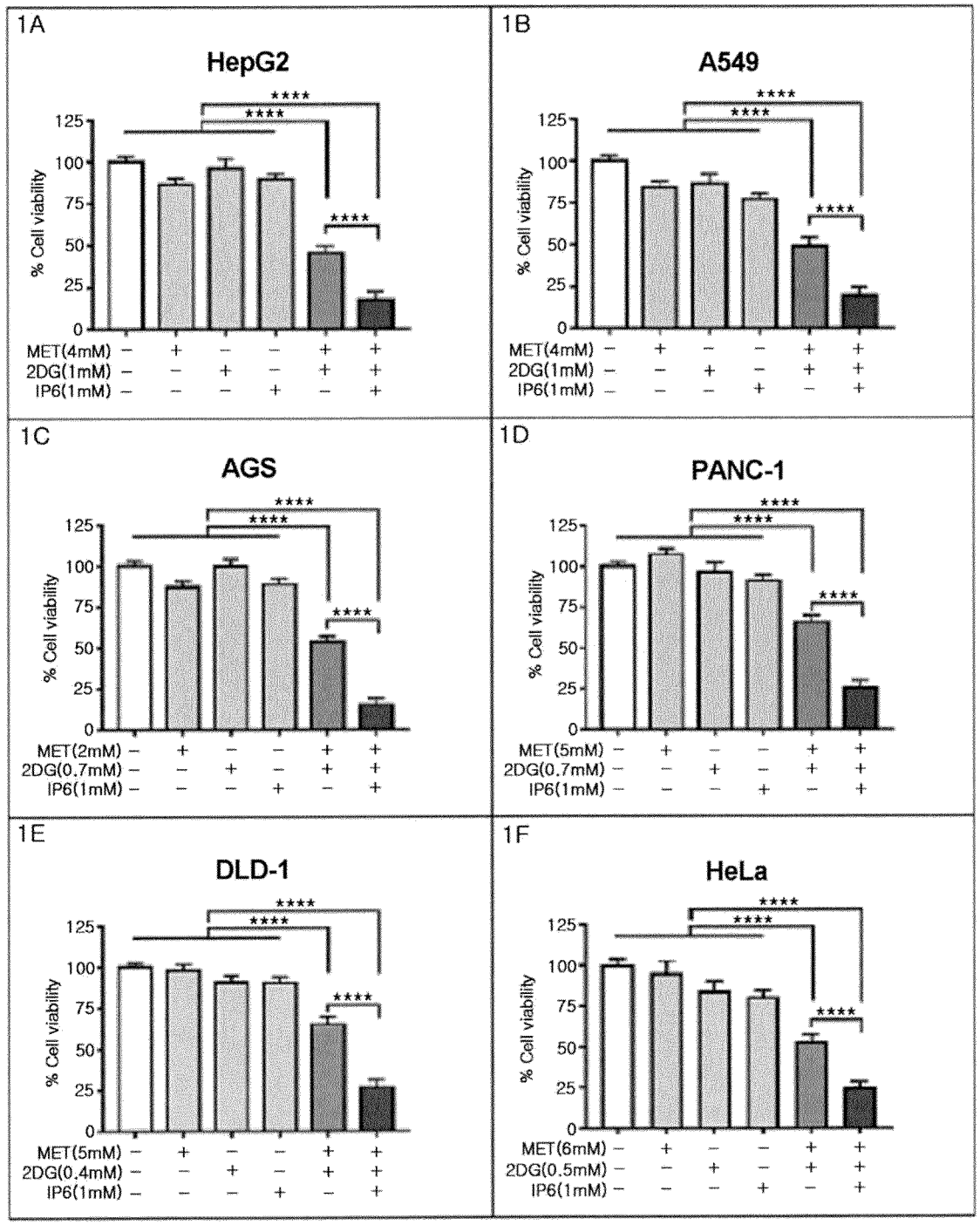

[Fig. 2]
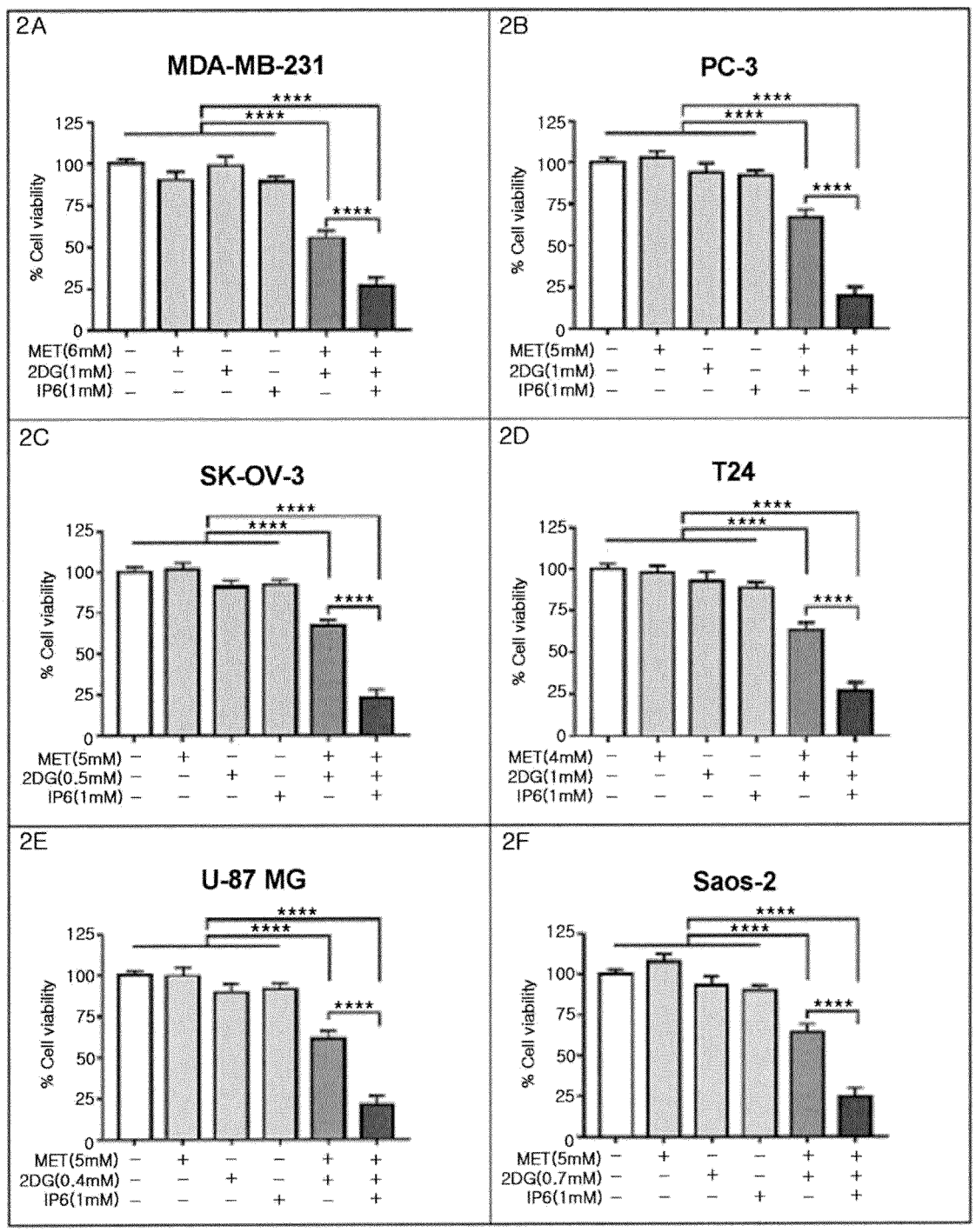

[Fig. 3]
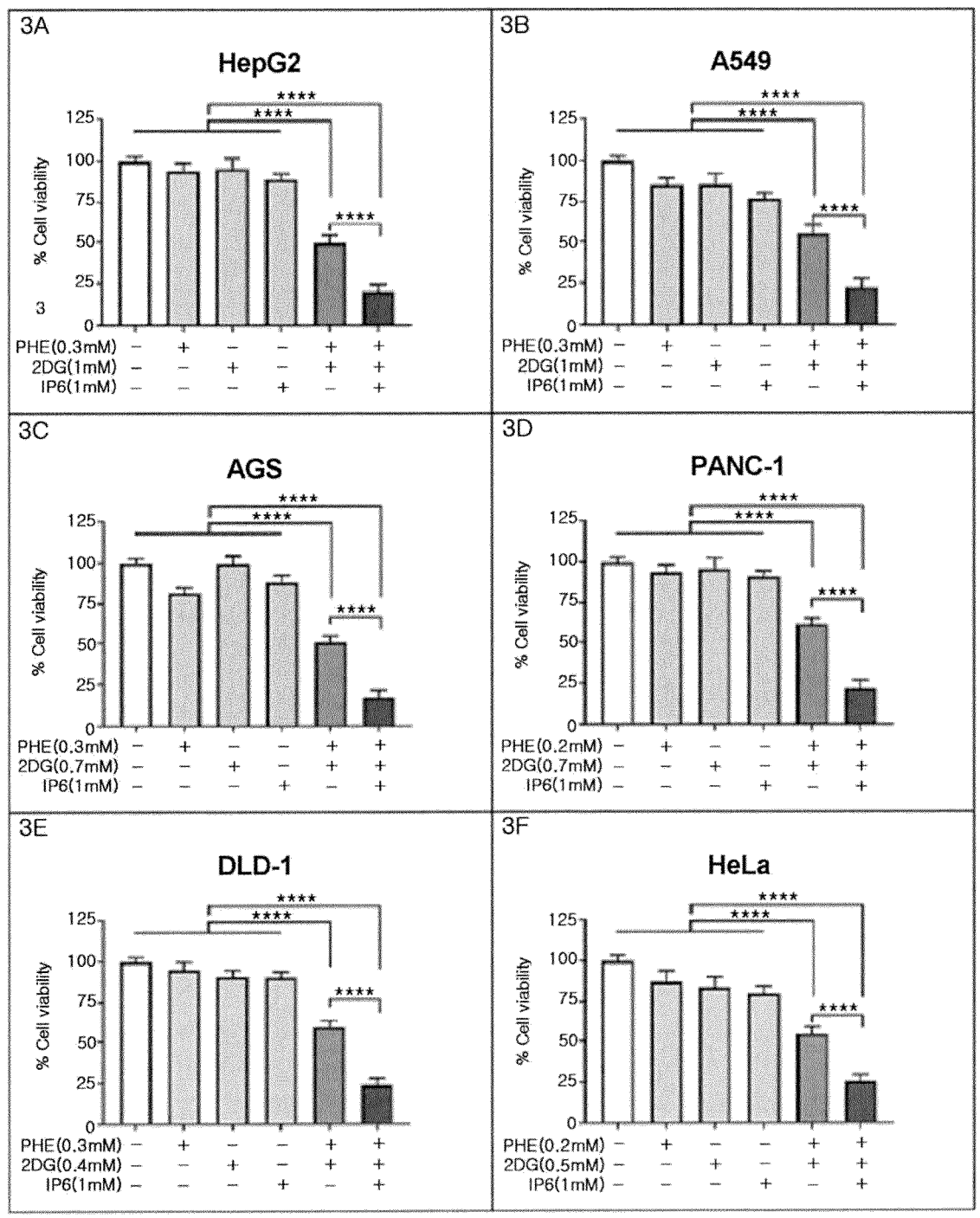

[Fig. 4]
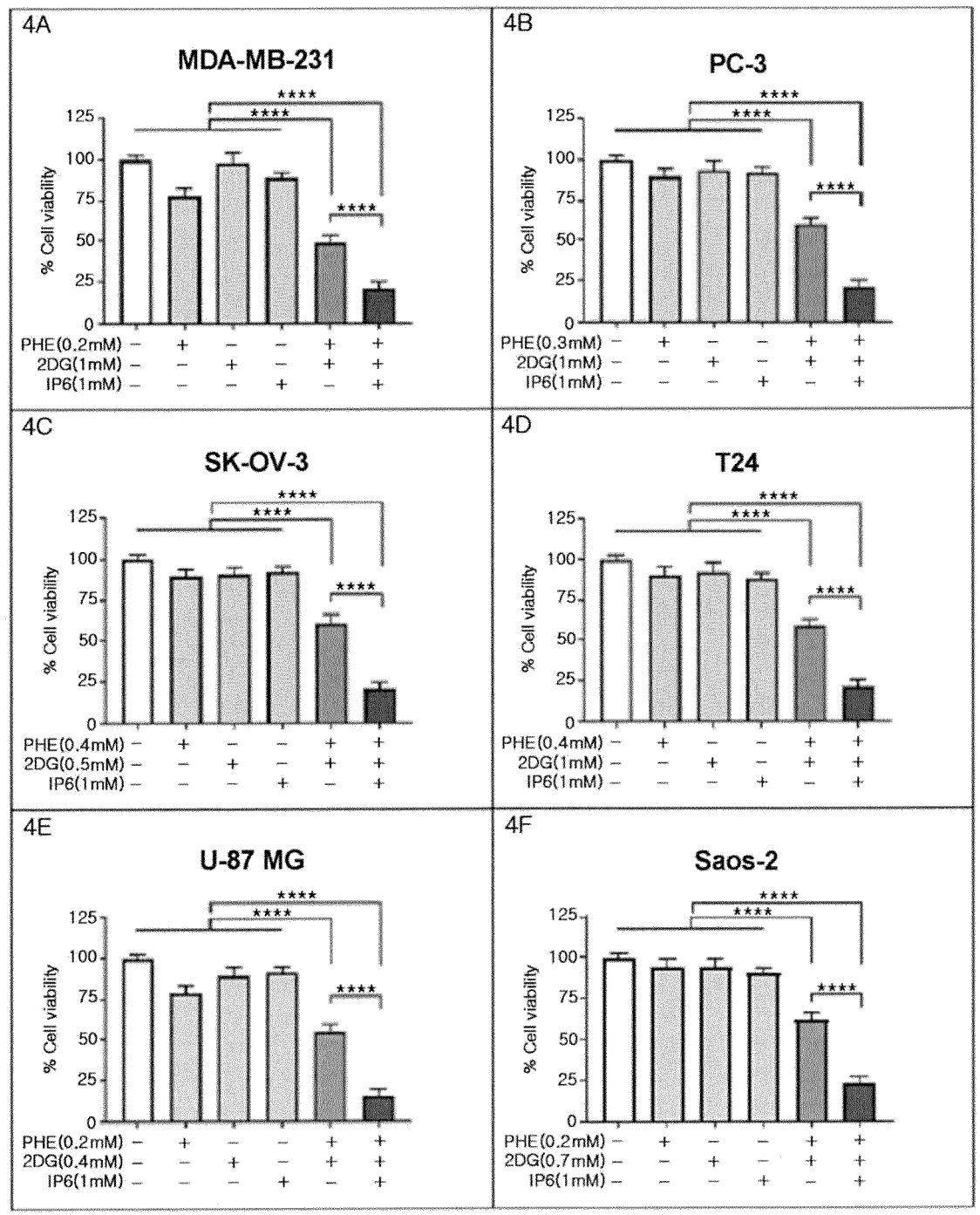

[Fig. 5]
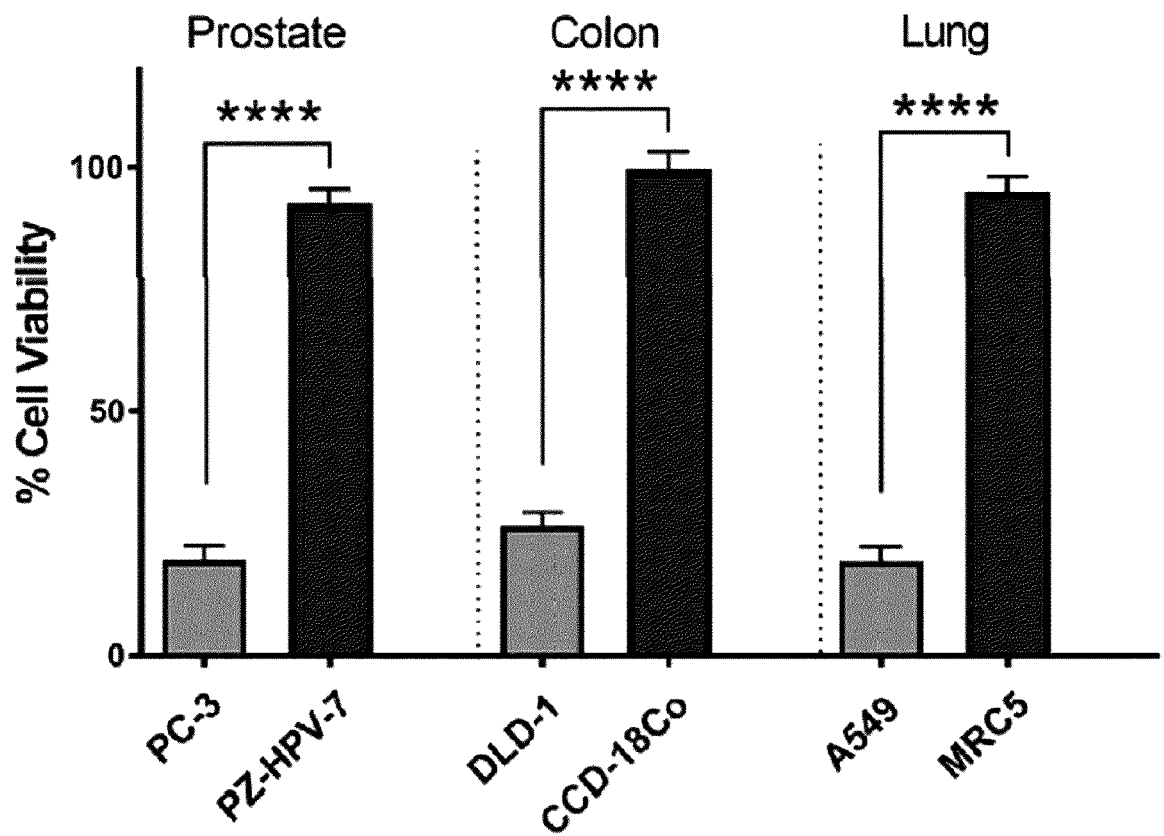

[Fig. 6]
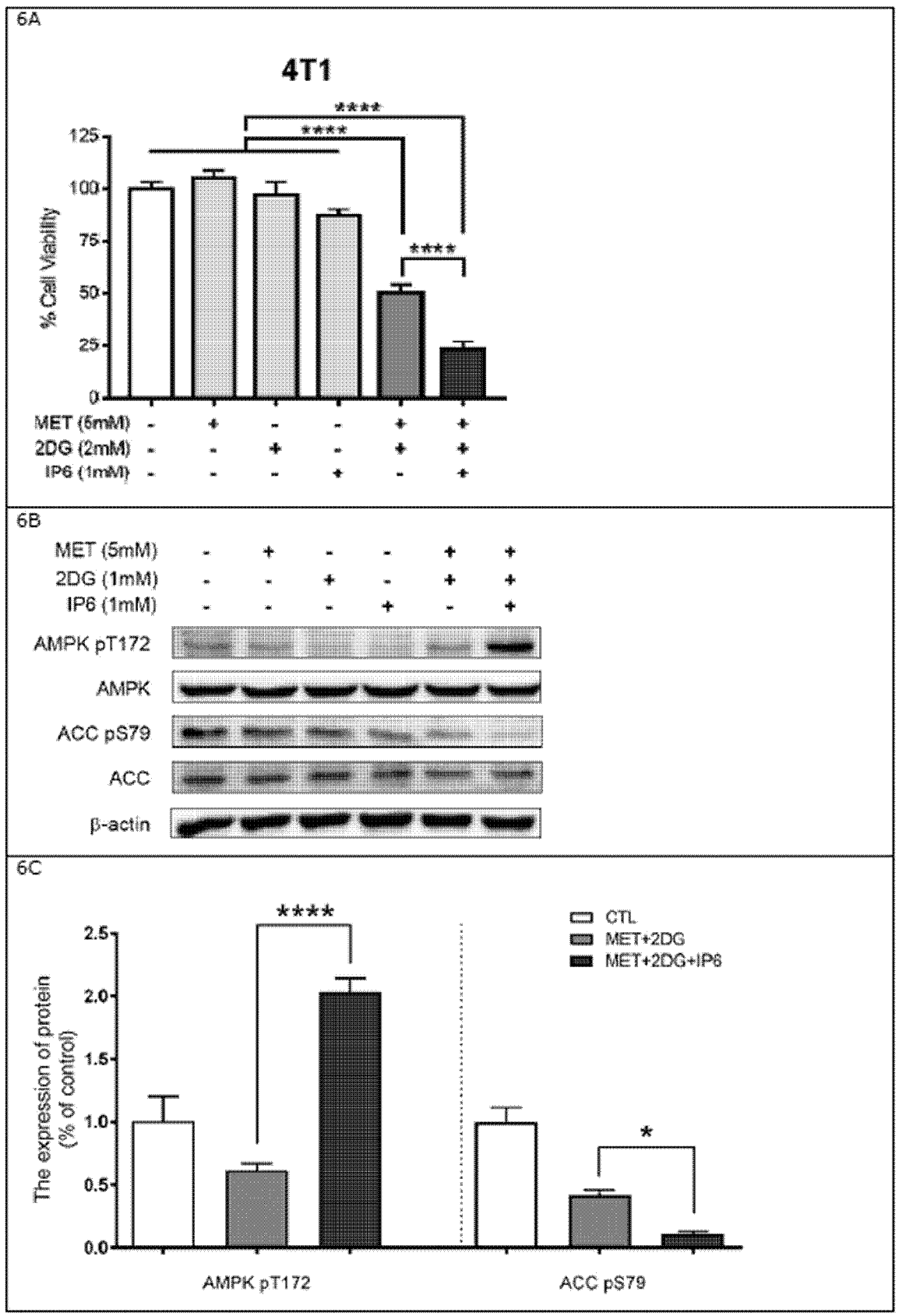

[Fig. 7]
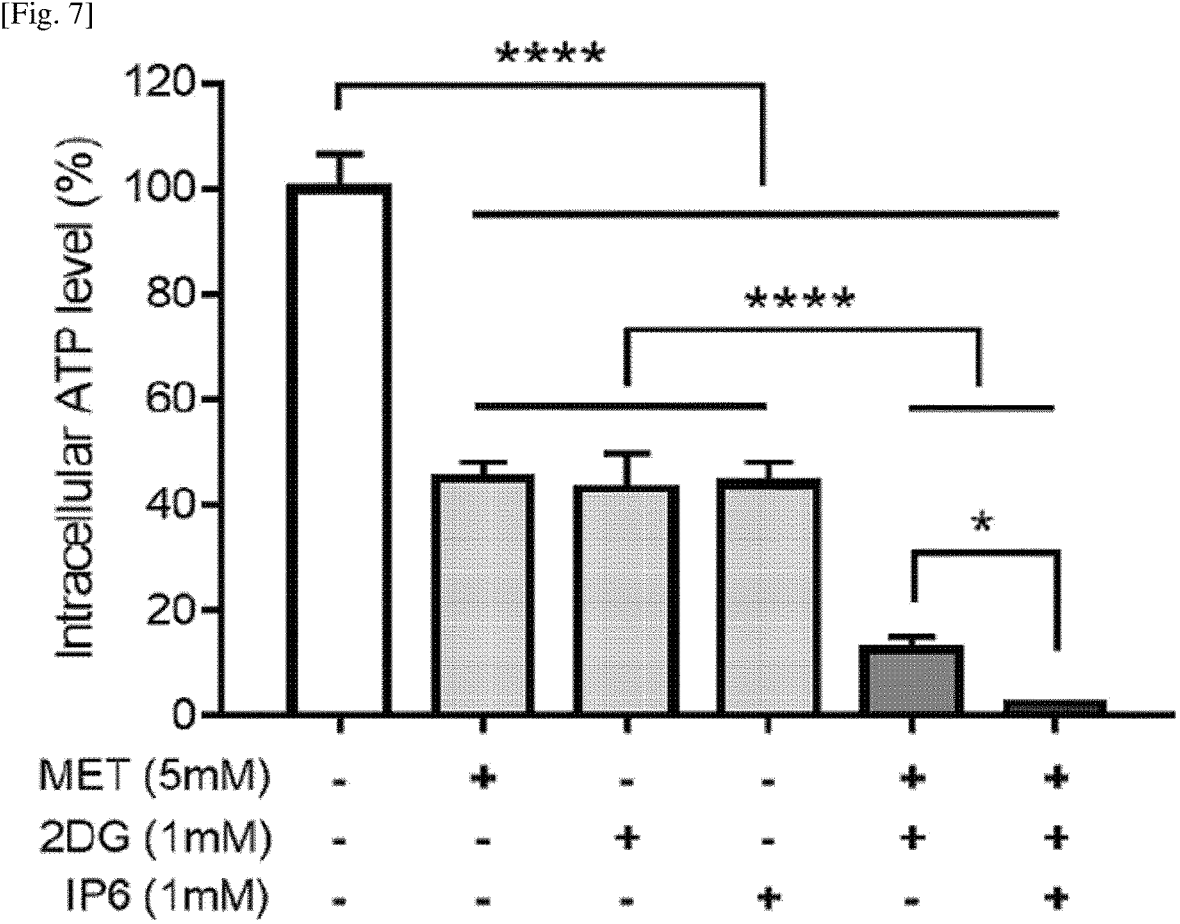

[Fig. 8]
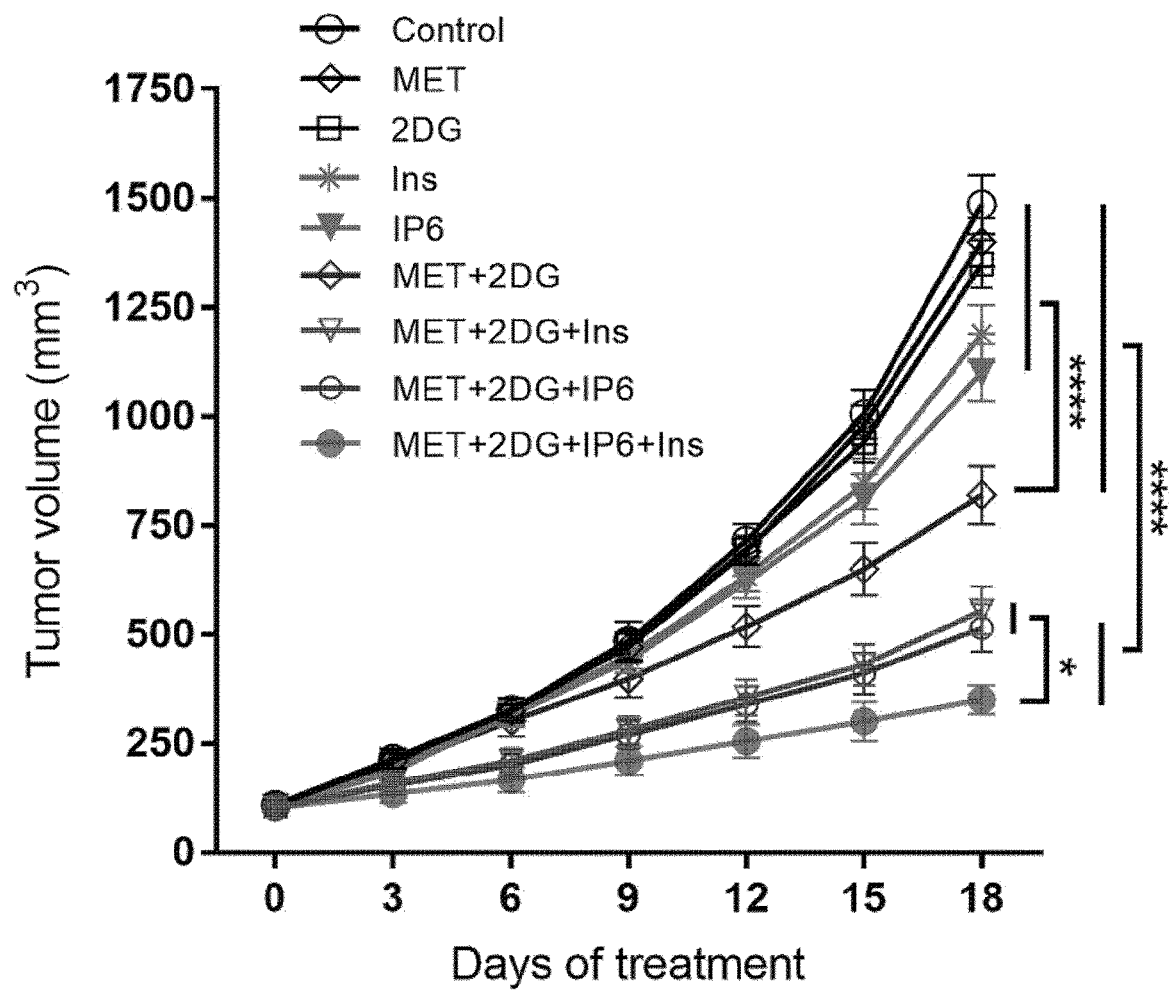

[Fig. 9]
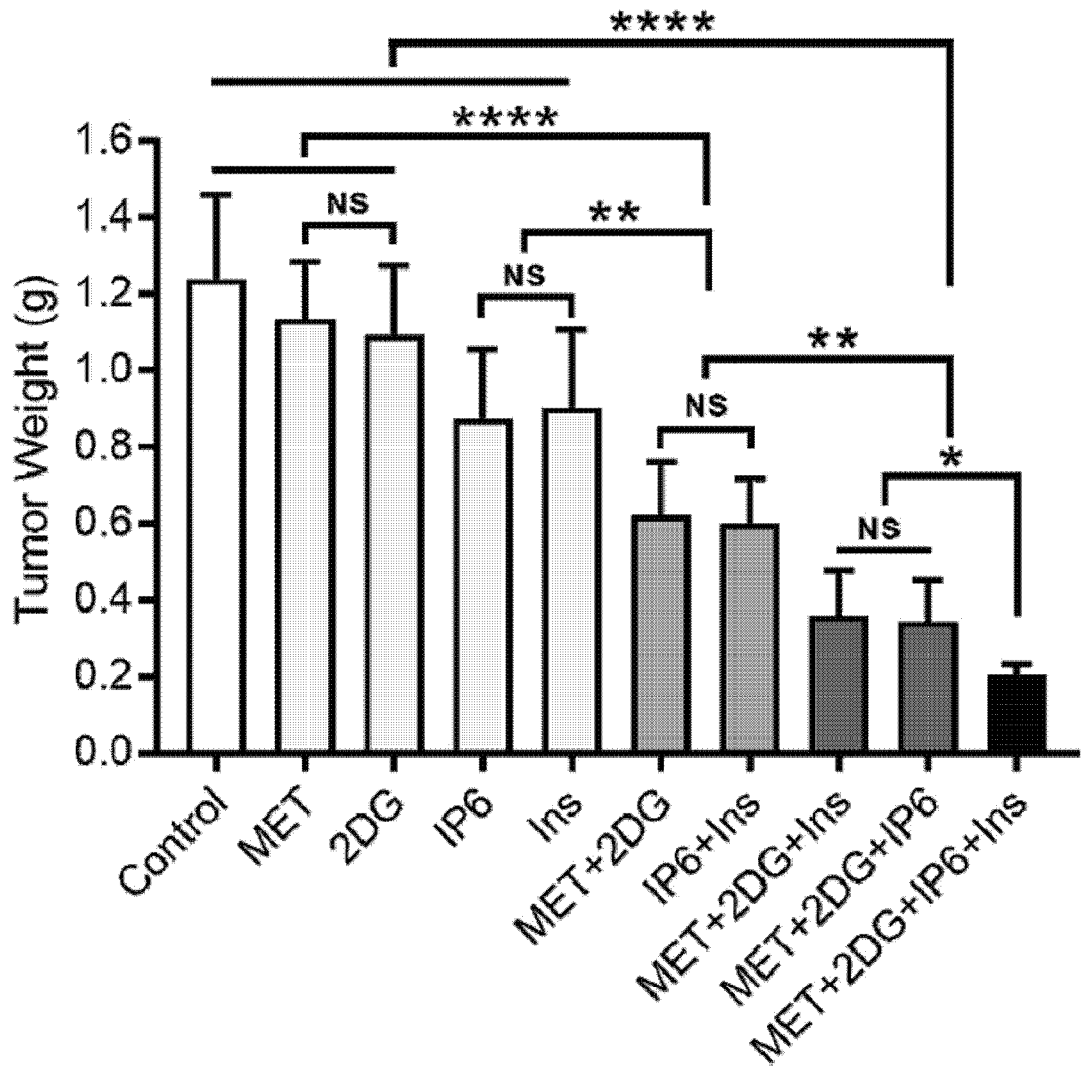

[Fig. 10]
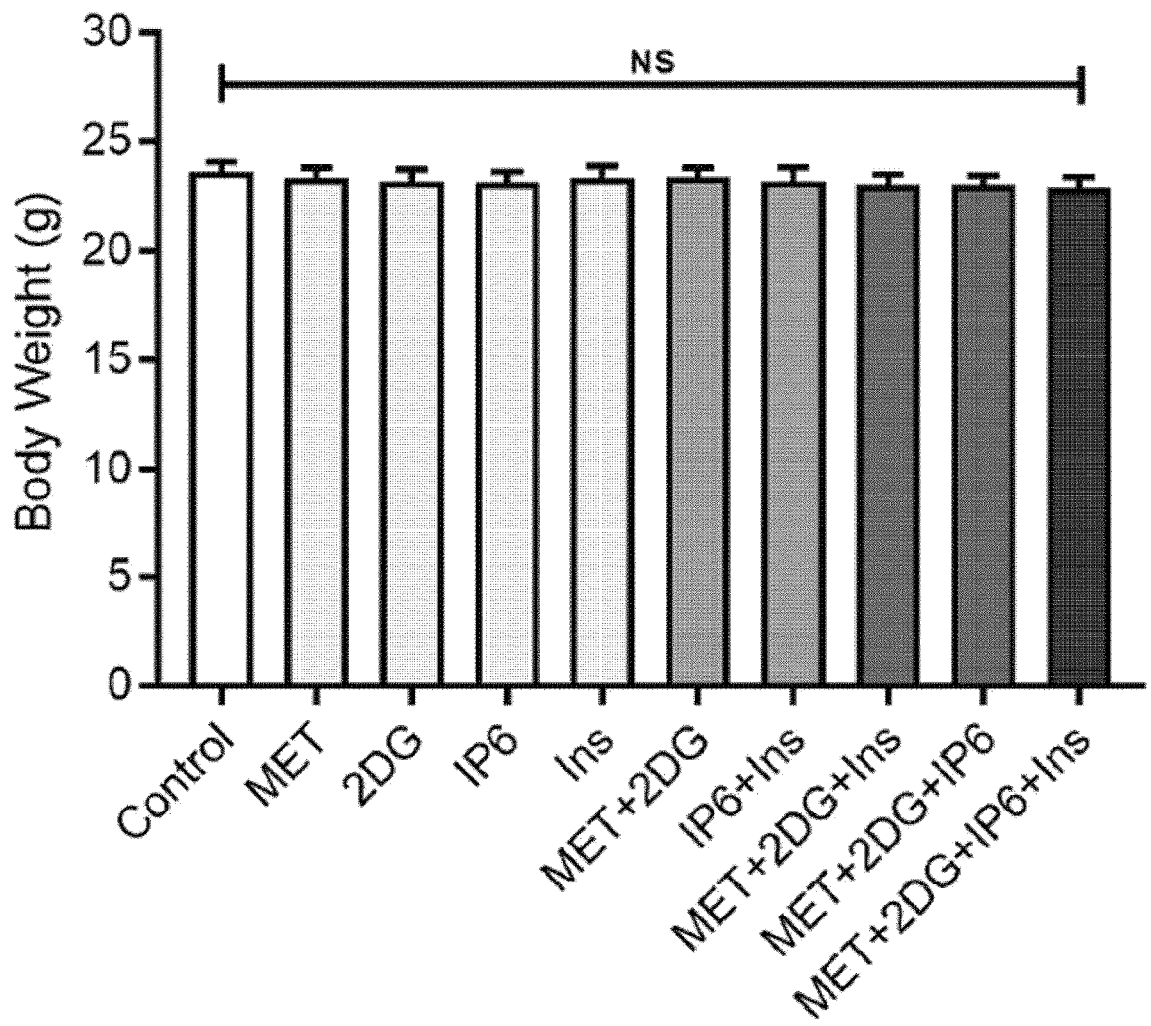

[Fig. 11]
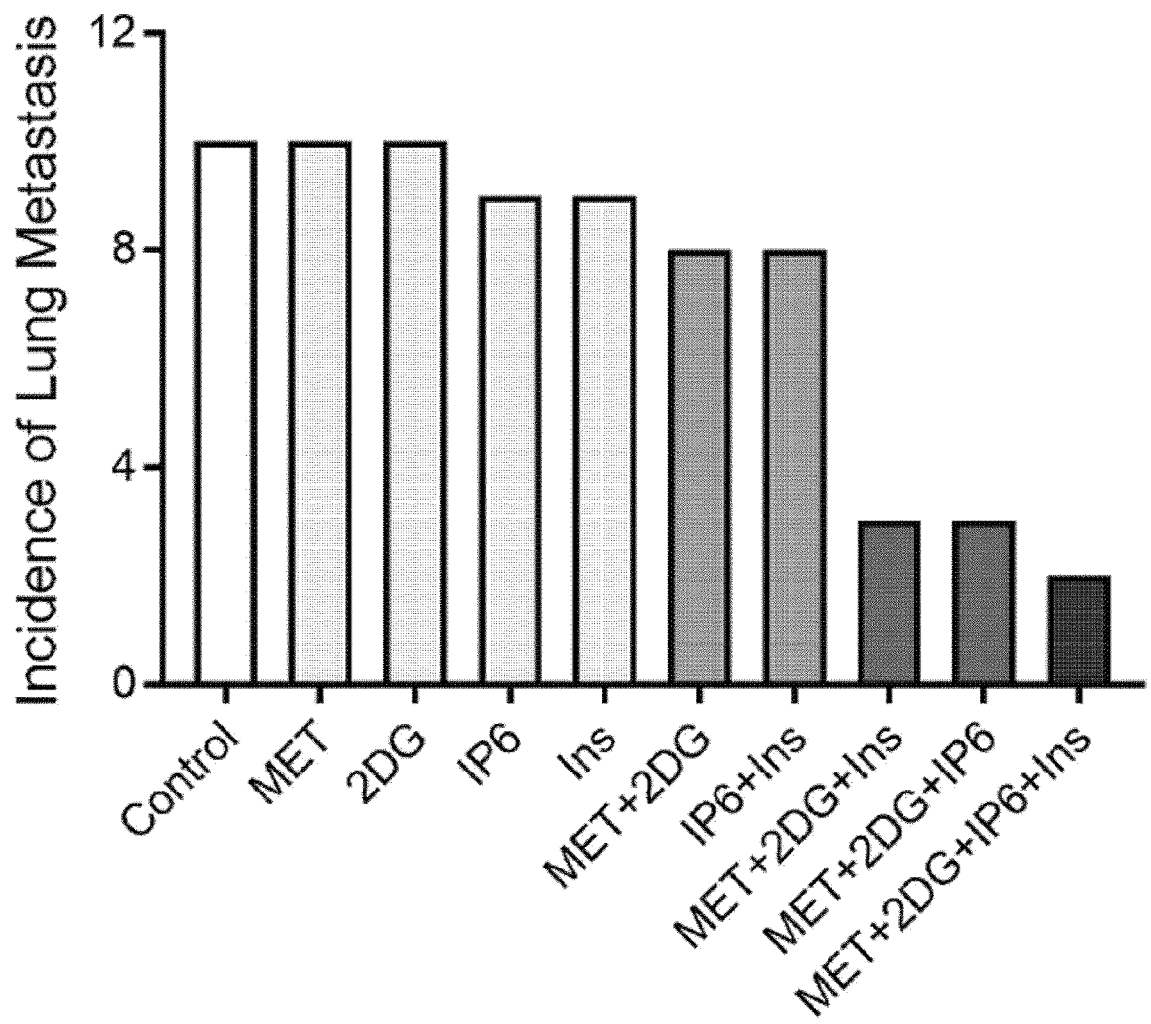

[Fig. 12]
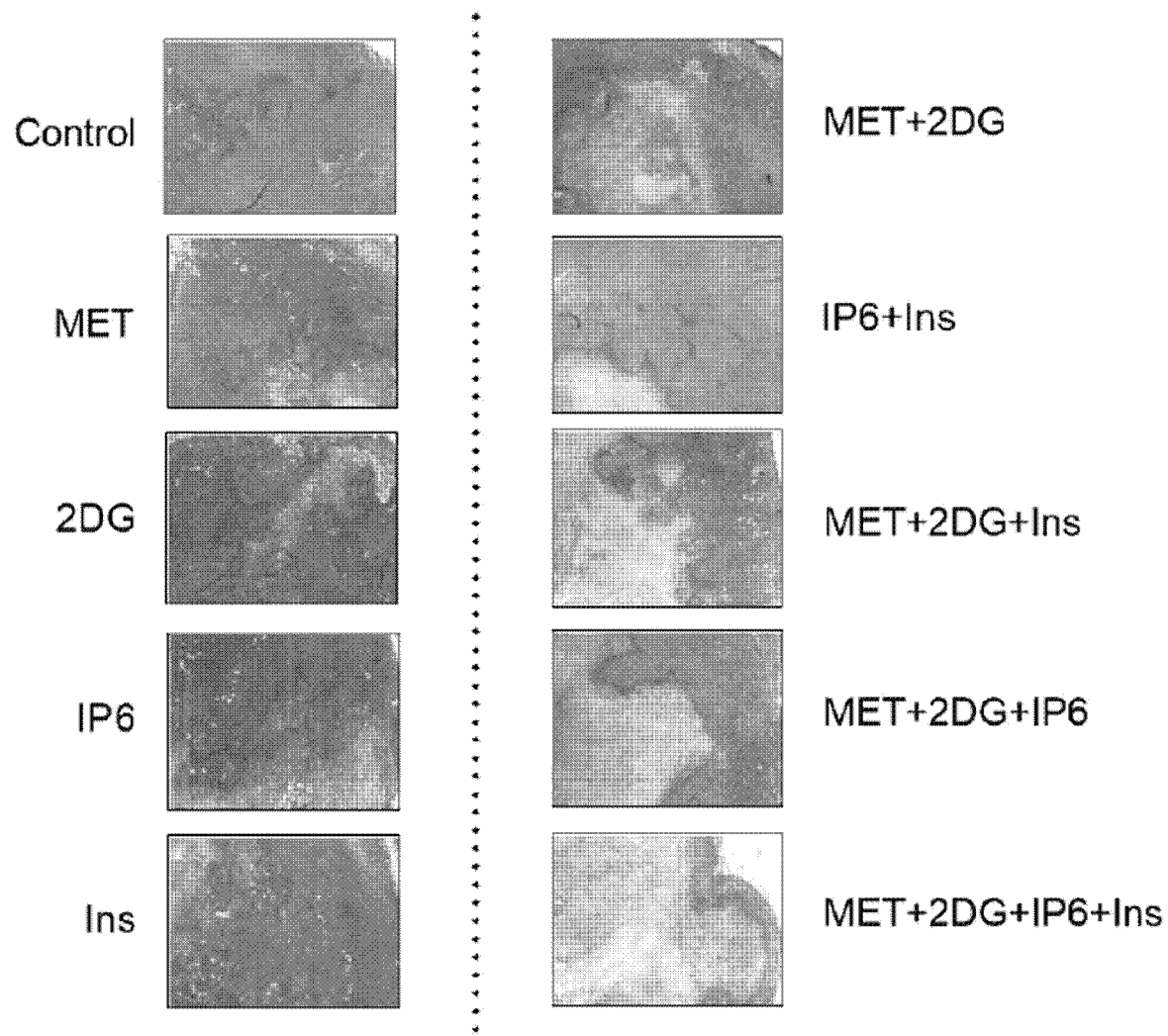

US 12,370,155 B2

ANTICANCER COMPOSITION

CROSS-REFERENCE TO RELATED APPLICATIONS

This is a U.S. National Phase of International Application No. PCT/KR2019/015251, filed Nov. 11, 2019, which claims priority to Korean Application No. 10-2018-0138345, filed Nov. 12, 2018, the contents of which are incorporated herein by reference.

TECHNICAL FIELD

The present invention relates to a pharmaceutical composition for preventing or treating cancer and a food composition for preventing or improving cancer comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

BACKGROUND ART

Chemotherapy is a treatment method that uses anticancer drugs to suppress and modify the growth of malignant tumors and has been used for 60 to 75% of cancer patients as first selective therapy or adjuvant therapy before and after surgery and radiation treatment, depending on the tumor.

When cancer is caused today, a combination of two or more treatments is the cornerstone of cancer treatment. While monotherapy is still widely used as a treatment method for various types of cancers, these conventional methods are generally less effective than combination therapies. Conventional monotherapy techniques selectively target actively proliferating cells, ultimately leading to the destruction of healthy and cancerous cells (Mokhtari et al., Oncotarget. 2017; 8: 38022-38043).

As such, chemotherapy exhibits toxicity to cells by involving in cancer cell metabolic pathways to interfere with DNA replication, transcription, and translation processes by direct interaction with DNA, disrupting the synthesis of nucleic acid precursors, and inhibiting cell division. Accordingly, the anticancer agent fatally damages normal cells to cause various side effects, such as hematocytopenia of leukocytes, platelets, and erythrocytes and the like caused by bone marrow destruction; hair loss due to hair follicle destruction; menstrual irregularities and male infertility as side effects on the ovaries and testes; stomatitis, nausea, vomiting and difficulty swallowing and digestive disorders as side effects from the destruction of mucous membrane cells of the digestive system; diarrhea symptoms; nephrotoxicity due to tubular necrosis; peripheral neuritis and weakness caused by nervous system disorders; vascular disorders such as vascular pain and rash and the like; and, skin and nail discoloration and the like. Therefore, research to increase the therapeutic effects while minimizing the side effects caused by anticancer drugs is urgently needed.

In addition, a main reason for the failure of chemotherapy is that the anticancer drug is effective initially, but gradually, drug resistance is expressed, and the immunity is extremely deteriorated. Therefore, there is a need for a method for improving the efficacy of cancer treatment without increasing the toxicity of the drug. The combination of anticancer drugs may be used as one method for improving the efficacy of the anticancer drugs, but unfortunately, combining anticancer drugs cannot all be expected to be synergistic, and finding a combination of drugs that have a synergistic effect is very difficult. Therefore, it is urgent to develop anticancer complex preparations that may maximize the anticancer effect while minimizing the side effects of anticancer drugs.

Recently, there has been much interest in developing anti-cancer therapies targeting cellular signal delivery pathways that are important for the metabolism and growth of cancer cells and representative drugs involving in the metabolism of the cancer cells includes metformin and 2-deoxy-D-glucose which are biguanide-based compounds (Wokoun et al., Oncol Rep. 2017; 37:2418-2424).

As an antihyperglycemic agent, metformin has been used as a first therapeutic agent for type 2 diabetes for decades. Despite the widespread use of metformin as an antidiabetic agent, potential anticancer effects in mammals were first reported in 2001. In addition, the first report on reducing cancer risk in patients with type 2 diabetes treated with metformin was published just 10 years ago. Since then, in many papers, metformin has shown consistent antiproliferative activity in several cancer cell lines including ovarian cancer, and xenotransplanted animals or transgenic mice. Regarding metabolism, metformin has been found as a new class of complex I and ATP synthase inhibitors, acts directly on mitochondria to restrict respiration and make energy inefficient and reduces glucose metabolism through citric acid circulation (Andrzejewski et al., 2014; 2: 12-25).

2-deoxy-D-glucose has been considered as a potential anticancer agent because of its dependence on tumor cells for glycolysis. 2-deoxy-D-glucose is a glucose analogue that can be easily absorbed by glucose transporters and acts as a competitive inhibitor of glycolysis, thereby reducing ATP production to induce cell death through activation of caspase-3 in solid tumors (Zhang et al., Cancer Lett. 2014; 355:176-183).

Studies have shown that a combination of two drugs, metformin and 2-deoxy-D-glucose, targeting two major cellular energy sources may have a significant advantage as compared with conventional chemotherapy alone. That is, metformin not only lowers blood sugar, but also blocks the respiratory chain in the mitochondria, which produces the energy needed for cellular activity, and 2-deoxy-D-glucose inhibits glucose degradation, so that the combination of the two drugs ultimately prevents an energy transfer process of cells. When these metabolic processes are activated, cancer cells are vulnerable to external attacks because energy to be supplied decreases even if energy consumption increases.

According to the reports for several tumor types, it has been known that the combination of metformin and 2-deoxy-D-glucose inhibits cell metabolism and causes tumor cell death, and the dose-dependently markedly reduction of survival of human breast cancer cells was caused by simultaneous metabolic disturbances in glycosylation (as 2-deoxy-D-glucose) and oxidative phosphorylation (as metformin) (Bizjak et al., Sci Rep. 2017; 7:1761-1774).

However, commonly used doses of metformin and 2-deoxy-D-glucose are insufficient to cure cancer sufficiently, and have a limitation in that adverse reactions may occur at high-dose treatment (Raez et al., Cancer Chemother Pharmacol. 2013; 71: 523-530). The combination treatment of metformin and 2-deoxy-D-glucose studied by Cheong et al. has been effective in breast cancer cell lines, but was higher than a concentration endurable in the human body or a concentration administrable in plasma (Cheong et al., Mol Cancer Ther. 2011; 10:2350-2362). In another paper, a combination of metformin and 2-deoxy-D-glucose has been successfully tested in prostate cancer cells using a metformin concentration higher than a concentration available in human plasma (Ben Sahra et al., Cancer Res. 2010; 70:2465-2475).

This suggests that it is preferred that clinically effective anticancer agents, metformin and 2-deoxy-D-glucose lower therapeutic concentrations thereof within a range that can be reasonably achieved in vivo.

Meanwhile, inositol hexaphosphate and inositol are naturally organic phosphorous compounds which are contained in large amounts in most grains, seeds, and legumes and present even in mammalian cells, and are present together with a phosphate form (IP1-5) with low phosphates. Inositol hexaphosphate plays an important role in regulating important cellular functions such as signal transduction, cell proliferation and differentiation of various cells and is recognized as a natural antioxidant (Shamsuddin et al., J Nutr. 2003; 133:3778S-3784S).

Recently, it has been reported that inositol hexaphosphate had some effects of preventing cancer and inhibiting the growth, progression and metastasis of experimental tumors (Vucenik et al., Nutr Cancer. 2006; 55:109-125).

In preliminary clinical studies, it is reported that inositol hexaphosphate and inositol are administered in combination with chemotherapy to reduce the side effects of chemotherapy and improve the quality of life in patients having breast or colorectal cancer, suffered with liver metastasis. However, it is still difficult to effectively suppress cancer cell growth only by using inositol hexaphosphate or a combination formulation of inositol hexaphosphate and inositol.

DISCLOSURE OF INVENTION

Technical Problem

Therefore, the present inventors have confirmed that when inositol hexaphosphate, inositol, or a mixture thereof was used as a complex formulation while biguanide-based compounds, metformin or phenformin and 2-deoxy-D-glucose were lowered to therapeutic concentrations that can reasonably be achieved in vivo, a cancer cell growth inhibition effect was significantly increased and completed the present invention. Since the present inventors confirmed that the complex formulation can effectively kill cancer cells even with a combination of low concentrations of the compounds, it is expected to be widely utilized in the field of cancer treatment in the future as well as securing the safety of the human body.

That is, an object of the present invention is to provide a pharmaceutical composition for preventing or treating cancer, which can effectively treat cancer even with a small amount of drugs and exhibits toxic effects on specific cancer cells, thereby reducing side effects.

Further, another object of the present invention is to provide a food composition for preventing or improving cancer.

Solution to Problem

As one aspect to achieve the objects, the present invention provides a pharmaceutical composition for preventing or treating cancer comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

As another aspect, the present invention provides a pharmaceutical composition for preventing or treating cancer comprising: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

As another aspect, the present invention provides a food composition for preventing or improving cancer comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

Hereinafter, the present invention will be described in detail.

In one aspect, the present invention relates to a pharmaceutical composition for preventing or treating cancer comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

In the present invention, by preparing a complex formulation comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof, an excellent anticancer agent capable of effectively treating cancer even with a small amount with fewer side effects has been developed.

The complex formulation of the present invention may use a smaller amount of individual compound included in the complex formulation than when treated with a single compound, thereby significantly reducing the risk and/or severity of side effects and significantly increasing the overall effect of the treatment.

In the present invention, the biguanide-based compound is, for example, metformin or phenformin. Specifically, metformin has a structural formula of Chemical Formula 1.

[Chemical Formula 1]

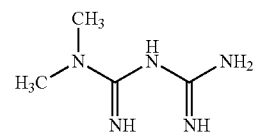

Specifically, phenformin has a structural formula of Chemical Formula 2.

[Chemical Formula 2]

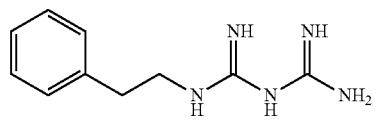

In the present invention, when (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof are used as a complex formulation, the compounds exhibit a high anticancer effect even at a low concentration.

The biguanide-based drugs are not limited thereto, but have an anticancer effect through an action mechanism that activates an enzyme called AMP-activated kinase (AMPK), which plays a pivotal role in intracellular energy balance and nutrient metabolic regulation.

When metformin is orally administered to rats, it can be seen that metformin, LD50 thereof is 1,450 mg/kg, is a very safe compound, but there is still a problem that metformin needs to be used in high doses. Meanwhile, phenformin was developed in the late 1950s as an oral diabetes treatment, and was intended to be used for the treatment of insulin-independent diabetes (type 2 diabetes), but due to a serious side effect called lactic acidosis, the use of phenformin was completely banned in the late 1970s.

In the present invention, a composition comprising at least three types of compounds was prepared using (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof as a complex formulation. It was confirmed that the composition exhibited a high anticancer effect even at a much lower concentration than that of each single agent or a composition of a combination of two compounds, thereby improving a problem of high-dose administration or a problem of side effects of metformin or phenformin (see FIGS. 1 to 4 and FIGS. 6 to 9).

In the present invention, 2-deoxy-D-glucose has a structure represented by the Chemical Formula 3.

[Chemical Formula 3]

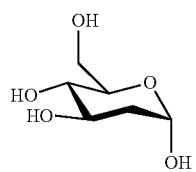

The compound of Chemical Formula 3 has an action effect as an inhibitor of glycolysis.

In the present invention, when 2-deoxy-D-glucose and a biguanide-based compound or a pharmaceutically acceptable salt thereof, and inositol hexaphosphate or a pharmaceutically acceptable salt thereof, inositol, or a mixture thereof is used as a complex formulation, it was confirmed that it had a high anticancer effect even at low concentrations. 2-deoxy-D-glucose, a derivative of glucose, has an action effect of inhibiting glycolysis in a glucose metabolism and inhibiting glycosylation of proteins in the endoplasmic reticulum to induce vesicle stress. As such, 2-deoxy-D-glucose, an inhibitor of glucose degradation, has not been shown to kill cancer cells by itself, but forms a complex formulation of the present invention to have excellent anticancer effects.

In the present invention, inositol hexaphosphate and/or inositol may regulate several important pathways in cancer cells. In the present invention, inositol hexaphosphate specifically has a structure of Chemical Formula 4.

[Chemical Formula 4]

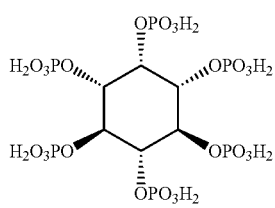

In the present invention, inositol specifically has a structure of Chemical Formula 5.

[Chemical Formula 5]

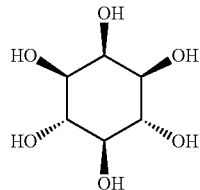

In the present invention, it was confirmed that inositol hexaphosphate or a pharmaceutically acceptable salt thereof, inositol, or a mixture thereof are combined with a biguanide-based compound or a pharmaceutically acceptable salt thereof and 2-deoxy-D-glucose to have a high anticancer effect even at a low concentration.

In the present invention, the biguanide-based compound and inositol hexaphosphate may be present in the form of a pharmaceutically acceptable salt. As the salt, acid addition salts formed with pharmaceutically acceptable free acids are useful. The term "pharmaceutically acceptable salt" used in the present invention refers to any organic or inorganic addition salt in which at a concentration having relatively non-toxic and harmless effects on a patient, side effects caused by the salt does not degrade a beneficial effect of the biguanide-based compound and inositol hexaphosphate.

At this time, as the addition salt, hydrochloric acid, phosphoric acid, sulfuric acid, nitric acid, tartaric acid, etc. may be used as inorganic acid, and methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. may be used as organic acid, but are not limited thereto.

Further, bases may also be used to prepare pharmaceutically acceptable metal salts. An alkali metal salt or an alkaline earth metal salt may be obtained, for example, by dissolving the compound in a large amount of alkali metal hydroxide or alkaline earth metal hydroxide solution, filtering a non-dissolved compound salt, and then evaporating and drying a filtrate. In this case, the metal salt is pharmaceutically suitable to prepare, particularly, sodium, potassium, calcium, and magnesium salts or mixed salts thereof, but is not limited thereto.

A pharmaceutically acceptable salt of each of the biguanide-based compound (metformin or phenformin) and inositol hexaphosphate may be a salt of acid or basic group which may be present in each of the biguanide-based compound (metformin or phenformin) and inositol hexaphosphate, unless otherwise indicated. For example, the pharmaceutically acceptable salt may include sodium, potassium, calcium or magnesium salts and the like of a hydroxy group, and other pharmaceutically acceptable salts of an amino group include hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate) salts and the like, which may be prepared through a method for preparing a salt known in the art.

As the salt of the biguanide-based compound (metformin or phenformin) of the present invention, as a pharmaceutically acceptable salt, any of metformin or phenformin salts exhibiting anticancer effects equivalent to metformin or phenformin may be used. Preferably, metformin hydrochloride, metformin succinate, metformin citrate or phenformin hydrochloride, phenformin succinate, phenformin citric acid and the like may be used, but are not limited thereto.

As the inositol hexaphosphate salt of the present invention, as a pharmaceutically acceptable salt, any inositol hexaphosphate salt exhibiting an anticancer effect equivalent to inositol hexaphosphate may be used. Preferably, inositol hexaphosphate sodium, inositol hexaphosphate potassium, inositol hexaphosphate calcium, inositol hexaphosphate ammonium, inositol hexaphosphate magnesium, inositol hexaphosphate calcium magnesium, and the like may be used, but are not limited thereto.

The biguanide-based compound, 2-deoxy-D-glucose, and inositol hexaphosphate of the present invention also include derivatives thereof. The term "derivative" refers to a compound prepared by chemically changing a part of the compound, for example, introduction, substitution, and deletion of a functional group, so long as the anticancer activity of the compound is not changed, and it can be included without limitation in the present invention.

In the present invention, inositol may exist in the form of various isomers. The isomers include both enantiomers and diastereomers. Any inositol that has a pharmacologically anticancer effect all may be used, and preferably, at least one selected from the group consisting of D-chiro-inositol, L-chiro-inositol, myo-inositol, and scylloinositol may be used, but is not limited thereto.

Even though combining two or more drugs, each of which is known to have an anticancer effect, it cannot be expected that the combined drug exhibits a synergistic effect, and rather, a function of the drug is offset by the combination, so that it is very difficult to find a combination of drugs having a synergistic effect. In the present invention, an anticancer complex formulation capable of maximizing the anticancer effect while minimizing side effects by using a minimum concentration of anticancer drugs has been developed.

In the present invention, a preferred aspect of the pharmaceutical composition for preventing or treating cancer may be a composition comprising a biguanide-based compound or a pharmaceutically acceptable salt thereof, 2-deoxy-D-glucose, and inositol hexaphosphate or a pharmaceutically acceptable salt thereof; a composition comprising a biguanide-based compound or a pharmaceutically acceptable salt thereof, 2-deoxy-D-glucose, and inositol; or a composition comprising a biguanide-based compound or a pharmaceutically acceptable salt thereof, 2-deoxy-D-glucose, and inositol hexaphosphate or a pharmaceutically acceptable salt thereof, and inositol.

In the present invention, the biguanide-based compound may be metformin or a pharmaceutically acceptable salt thereof, or phenformin or a pharmaceutically acceptable salt thereof.

When describing a composition centered on metformin as the biguanide-based compound, the pharmaceutical composition for preventing or treating cancer may be a composition comprising metformin or a pharmaceutically acceptable salt thereof, 2-deoxy-D-glucose, and inositol hexaphosphate or a pharmaceutically acceptable salt thereof; a composition comprising metformin or a pharmaceutically acceptable salt thereof, 2-deoxy-D-glucose, and inositol; or a composition comprising metformin or a pharmaceutically acceptable salt thereof, 2-deoxy-D-glucose, and inositol hexaphosphate or a pharmaceutically acceptable salt thereof, and inositol.

When describing a composition centered on phenformin as another biguanide-based compound, the composition for preventing or treating cancer may be a composition comprising phenformin or a pharmaceutically acceptable salt thereof, 2-deoxy-D-glucose, and inositol hexaphosphate or a pharmaceutically acceptable salt thereof; a composition comprising phenformin or a pharmaceutically acceptable salt thereof, 2-deoxy-D-glucose, and inositol; or a composition comprising phenformin or a pharmaceutically acceptable salt thereof, 2-deoxy-D-glucose, and inositol hexaphosphate or a pharmaceutically acceptable salt thereof, and inositol.

In one embodiment of the present invention, it was confirmed that a complex formulation consisting of a biguanide-based compound or a pharmaceutically acceptable salt thereof, 2-deoxy-D-glucose, and inositol hexaphosphate or a pharmaceutically acceptable salt thereof may inhibit cell proliferation of cancer cell lines in vitro (Example 1).

Further, in the case of using a complex formulation consisting of three or more compounds constituted by a composition comprising a biguanide-based compound or a pharmaceutically acceptable salt thereof, 2-deoxy-D-glucose, and inositol hexaphosphate or a pharmaceutically acceptable salt thereof; a composition comprising a biguanide-based compound or a pharmaceutically acceptable salt thereof, 2-deoxy-D-glucose, and inositol; or a composition comprising a biguanide-based compound or a pharmaceutically acceptable salt thereof, 2-deoxy-D-glucose, inositol hexaphosphate or a pharmaceutically acceptable salt thereof, and inositol, due to the combination of the compounds, it was confirmed that a synergistic effect of preventing or treating cancer was shown in vivo and a cancer suppression concentration was significantly reduced (Examples 5 to 9).

That is, according to the present invention, in the case of using each of the biguanide-based compound, 2-deoxy-D-glucose, inositol hexaphosphate and inositol alone, a large amount thereof needs to be used due to insufficient anticancer effects, but when a complex formulation combining the compounds is used, it was confirmed that cancer cells may be effectively killed even in a small amount.

In particular, a complex formulation of metformin/2-deoxy-D-glucose/inositol hexaphosphate, a complex formulation of metformin/2-deoxy-D-glucose/inositol, and a complex formulation of metformin/2-deoxy-D-glucose/inositol hexaphosphate/inositol showed a much higher effect of reducing a cancer suppression concentration than a single formulation of each compound or a complex formulation of two compounds such as metformin/2-deoxy-D-glucose.

In each complex formulation according to the present invention, a weight ratio of the combination of each compound is not particularly limited.

For example, a weight ratio of metformin or a pharmaceutically acceptable salt thereof: 2-deoxy-D-glucose: inositol hexaphosphate or a pharmaceutically acceptable salt thereof may be a range of 1:0.2:0.5 to 1:5:20, and a relative amount of combination may vary depending on a type of cancer to be treated.

In another example, a weight ratio of phenformin or a pharmaceutically acceptable salt thereof: 2-deoxy-D-glucose: inositol hexaphosphate or a pharmaceutically acceptable salt thereof may be a range of 1:1:1 to 1:50:200, and a relative amount of combination may vary depending on a type of cancer to be treated.

In another example, a weight ratio of metformin or a pharmaceutically acceptable salt thereof: 2-deoxy-D-glucose: inositol may be a range of 1:0.2:0.5 to 1:5:20, and a relative amount of combination may vary depending on a type of cancer to be treated.

In another example, a weight ratio of phenformin or a pharmaceutically acceptable salt thereof: 2-deoxy-D-glucose: inositol may be a range of 1:1:1 to 1:50:200, and a relative amount of combination may vary depending on a type of cancer to be treated.

In another example, a weight ratio of metformin or a pharmaceutically acceptable salt thereof: 2-deoxy-D-glucose: inositol hexaphosphate or a pharmaceutically acceptable salt thereof: inositol may be a range of 1:0.2:0.5:0.5 to 1:5:20:20, and a relative amount of combination may vary depending on a type of cancer to be treated.

In another example, a weight ratio of phenformin or a pharmaceutically acceptable salt thereof: 2-deoxy-D-glucose: inositol hexaphosphate or a pharmaceutically acceptable salt thereof: inositol may be a range of 1:1:1:1 to 1:50:200:200, and a relative amount of combination may vary depending on a type of cancer to be treated. In the present invention, the term "cancer" refers to a disease associated with cell death control, and refers to a disease caused by excessive proliferation of cells when a normal apoptotic balance is broken. These abnormally overproliferating cells invade surrounding tissues and organs to form masses in some cases and destroy or modify the normal structure of the body, which is called cancer. In general, the term "tumor" refers to a mass grown abnormally by autonomous overgrowth of body tissues, and may be classified into a benign tumor and a malignant tumor. The malignant tumor grows much faster than benign tumor, and invades surrounding tissues, as a result, metastasis occurs to threaten the life. The malignant tumor is commonly referred to as 'cancer', and the types of cancer include cerebral spinal cord tumor, brain cancer, head and neck cancer, lung cancer, breast cancer, thymic tumor, esophageal cancer, stomach cancer, colon cancer, liver cancer, pancreatic cancer, biliary tract cancer, kidney cancer, bladder cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer, and the like. The anticancer composition of the present invention may be used without limitation to the type of cancer, but may be used for preventing or treating at least one selected from the group consisting of liver cancer, lung cancer, stomach cancer, pancreatic cancer, colon cancer, cervical cancer, breast cancer, prostate cancer, ovarian cancer, brain cancer, osteosarcoma and bladder cancer.

The term "preventing or treating" used in the present invention refers to all actions that inhibit or delay the development of cancer using the composition comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof, and particularly, "treating" refers to all actions of improving or beneficially modifying cancer using the composition.

Therefore, the present invention provides a method for treating cancer comprising administering a therapeutically effective amount of (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof to a subject in need of treatment thereof.

The term "administering" used in the present invention refers to providing a subject with the composition according to the present invention in any suitable manner. At this time, the subject refers to an animal, and may be a mammal that can exhibit a beneficial effect, typically with treatment with the composition according to the present invention. Preferred examples of such individuals may include primates such as humans.

The composition for preventing or treating cancer of the present invention may further include a chemotherapeutic agent for treating cancer, if necessary, in addition to the above-mentioned active ingredients.

In addition, the composition for preventing or treating cancer of the present invention may further include a pharmaceutically acceptable carrier. The composition of the present invention, according to the purpose of use, may be formulated and used by oral formulation such as powders, granules, tablets, capsules, suspensions, emulsions, syrups, and aerosols and the like, sterile injectable solutions, external forms such as ointments and the like, and suppositories and the like according to general methods. A carrier, an excipient, and a diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil and the like.

A solid formulation for oral administration includes a tablet, a pill, a powder, a granule, a capsule, and the like, and such solid formulation may be formulated by mixing at least one excipient, for example, starch, calcium carbonate, sucrose, lactose, gelatin, and the like with the composition. Further, lubricants such as magnesium stearate and talc may also be used in addition to simple excipients. A liquid formulation for oral administration may correspond to a suspension, an internally applied solution, an emulsion, a syrup, and the like, and may include various excipients, for example, a wetting agent, a sweetener, an aromatic agent, a preserving agent, and the like in addition to water and liquid paraffin which are commonly used as simple diluents.

A formulation for parenteral administration includes a sterile aqueous solution, a non-aqueous solution, a suspension, an emulsion, and a lyophilizing agent, and a suppository. As the non-aqueous solution and the suspension, propylene glycol, polyethylene glycol, vegetable oil such as olive oil, injectable ester such as ethyl oleate, and the like may be used. Bases for the injectable agent may include conventional additives such as solubilizers, isotonic agents, suspending agents, emulsifiers, stabilizers and preservatives.

The composition of the present invention may be administered using a variety of methods, such as oral, intravenous, subcutaneous, intradermal, intranasal, intraperitoneal, intramuscular, and transdermal administration and the like, and the dosage may vary depending on the age, gender, and weight of the patient and may be easily determined by those skilled in the art. The dosage of the composition according to the present invention may be increased or decreased depending on a route of administration, the severity of the disease, gender, weight, age, and the like. Preferably, in the case of a complex formulation of four compounds, metformin as the biguanide-based compound may be used with 5 to 80 mg/kg (body weight) per day, phenformin may be used with 0.1 to 10 mg/kg (body weight) per day, 2-deoxy-D-glucose may be used with 0.1 to 160 mg/kg (body weight) per day, inositol hexaphosphate may be used with 2 to 600 mg/kg (body weight) per day, and inositol may be used with 2 to 600 mg/kg (body weight) per day. However, the scope of the present invention is not limited by the dosage.

As another aspect, the present invention relates to a method for treating cancer comprising administering, to a subject, (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

As yet another aspect, the present invention relates to a composition for use in the treatment of cancer comprising: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

As still another aspect, the present invention relates to a use of composition comprising: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof for preparing a drug for preventing or treating cancer.

As still yet another aspect, the present invention relates to a food composition for preventing or improving cancer comprising, as active ingredients: (1) a biguanide-based compound or a pharmaceutically acceptable salt thereof; (2) 2-deoxy-D-glucose; and (3) inositol hexaphosphate or a pharmaceutically acceptable salt thereof, inositol, or a mixture thereof.

The biguanide-based compound may be metformin or phenformin.

The composition may include a food acceptable food supplement additives in addition to the active ingredients.

The term "food supplement additive" used in the present invention means a component that may be supplementally added to food, and may be appropriately selected and used by those skilled in the art as being added to prepare a health functional food of each formulation. Examples of the food supplement additives include various nutrients, vitamins, minerals (electrolytes), flavors such as synthetic and natural flavors and the like, colorants and fillers, pectic acid and salts thereof, alginic acid and salts thereof, organic acids, protective colloidal thickeners, pH adjusters, stabilizers, preservatives, glycerin, alcohols, and carbonation agents used in carbonated drinks, and the like, but the types of supplement additives of the present invention are not limited by the above examples.

The food composition of the present invention may include a health functional food.

The term "health functional food" used in the present invention refers to food prepared and processed in the form of tablets, capsules, powders, granules, liquids and pills and the like using raw materials or ingredients having functionalities useful to the human body. Here, the 'functionality' refers to the adjustment of nutrients to the structure and function of the human body or to obtainment of effects useful for health applications such as physiological action and the like. The health functional food of the present invention may be prepared by methods which are commonly used in the art and may be prepared by adding raw materials and ingredients which are commonly added in the art in preparation. In addition, the formulation of the health functional food may also be prepared without limitation as long as the formulation is recognized as a health functional food. The food composition of the present invention may be prepared in various types of formulations, and unlike general drugs, the food composition made from food as raw material has an advantage that there is no side effect that may occur when taking a long-term use of the drug, and has excellent portability, and the health functional food of the present invention can be taken as supplements to enhance the effects of anticancer drugs.

Advantageous Effects of Invention

The composition of the present invention exhibits a synergistic anticancer effect by appropriately combining specific drugs having a problem that needs to be used in a large amount, thereby making it possible to kill cancer cells in a small amount and effectively treat the cancer. Furthermore, the composition of the present invention may kill only cancer cells without side effects by exhibiting a specific toxic effect on cancer cells without showing toxicity on normal cells and thus may be usefully used as an anticancer agent and for preventing or improving cancer.

BRIEF DESCRIPTION OF DRAWINGS

FIGS. 1 and 2 are graphs showing cell survival rate by MTT assay as a percentage after 48 hours by treating single and complex formulations of metformin (MET), 2-deoxy-D-glucose (2DG) and inositol hexaphosphate (IP6) to human-derived cancer cell lines at a low concentration usable in human plasma. A vertical bar of each bar represents a standard deviation. Statistical analysis was performed by one-way ANOVA testing using Tukey's multiple comparison post analysis using GraphPad Prism 6.0 software.

FIG. 1A is a graph of examining a HepG2 cell line as cancer cells derived from human liver. FIG. 1B is a graph of examining an A549 cell line as cancer cells derived from human lung. FIG. 1C is a graph of examining an AGS cell line as cancer cells derived from human stomach. FIG. 1D is a graph of examining a PANC-1 cell line as cancer cells derived from human pancreas. FIG. 1E is a graph of examining a DLD-1 cell line as cancer cells derived from human colon. FIG. 1F is a graph of examining a HeLa cell line as cancer cells derived from human cervix. FIG. 2A is a graph of examining an MDA-MB-231 cell line as cancer cells derived from human breast. FIG. 2B is a graph of examining a PC-3 cell line as cancer cells derived from human prostate. FIG. 2C is a graph of examining an SK-OV-3 cell line as cancer cells derived from human ovary. FIG. 2D is a graph of examining a T24 cell line as cancer cells derived from human bladder. FIG. 2E is a graph of examining a U-87 MG cell line as cancer cells derived from human brain. FIG. 2F is a graph of examining a Saos-2 cell line as cancer cells derived from human bones. ****$p<0.0001$.

FIGS. 3 and 4 are graphs showing cell survival rate by MTT assay as a percentage after 48 hours by treating single and complex formulations of phenformin (PHE), 2DG, and IP6 to human-derived cancer cell lines at a low concentration usable in human plasma. A vertical bar of each bar represents a standard deviation. Statistical analysis was performed by one-way ANOVA testing using Tukey's multiple comparison post analysis using GraphPad Prism 6.0 software.

FIG. 3A is a graph of examining a HepG2 cell line as cancer cells derived from human liver. FIG. 3B is a graph of examining an A549 cell line as cancer cells derived from human lung. FIG. 3C is a graph of examining an AGS cell line as cancer cells derived from human stomach. FIG. 3D is a graph of examining a PANC-1 cell line as cancer cells derived from human pancreas. FIG. 3E is a graph of examining a DLD-1 cell line as cancer cells derived from human colon. FIG. 3F is a graph of examining a HeLa cell line as cancer cells derived from human cervix. FIG. 4A is a graph of examining an MDA-MB-231 cell line as cancer cells derived from human breast. FIG. 4B is a graph of examining a PC-3 cell line as cancer cells derived from human prostate. FIG. 4C is a graph of examining an SK-OV-3 cell line as cancer cells derived from human ovary. FIG. 4D is a graph of examining a T24 cell line as cancer cells derived from human bladder. FIG. 4E is a graph of examining a U-87 MG cell line as cancer cells derived from human brain. FIG. 4F is a graph of examining a Saos-2 cell line as cancer cells derived from human bones. ****$p<0.0001$.

FIG. 5 is a graph showing cell survival rate by MTT assay as a percentage after 48 hours by treating a complex formulation of MET, 2DG, and IP6 to human-derived normal cell lines at a low concentration usable in human plasma. ****$p<0.0001$.

FIG. 6 is a diagram showing the cell survival rate and protein expression in 4T1 cells using single and complex formulations of MET, 2DG and IP6. *$p<0.05$. ****$p<0.0001$.

FIG. 7 is a graph of ATP synthesis inhibition of single and complex formulations of MET, 2DG and IP6 for 4T1 cells. *$p<0.05$. ****$p<0.0001$.

FIG. 8 is a graph of tumor volumes measured at three-day intervals according to administration of single and complex formulations of MET, 2DG, IP6 and Ins in a test animal. *$p<0.05$, ****$p<0.0001$.

FIG. 9 is a graph of tumor weights measured on day 19 after administration of single and complex formulations of MET, 2DG, IP6 and Ins in a test animal. *$p<0.05$, $p<0.01$, **$p<0.0001$.

FIG. 10 is a graph of weights measured on day 18 after administration of single and complex formulations of MET, 2DG, IP6 and Ins in a test animal. NS (no significant difference).

FIG. 11 is a graph of examining the incidence of lung metastasis of single and complex formulations of MET, 2DG, IP6 and Ins.

FIG. 12 is a diagram of hematoxylin & eosin staining for examining effects of single and complex formulations of MET, 2DG, IP6 and Ins on histomorphologic changes of tumor tissues.

MODE FOR THE INVENTION

Advantages and features of the present invention, and methods for accomplishing the same will be apparent with reference to the embodiments described below in detail. However, the present invention is not limited to the following exemplary embodiments but may be implemented in various different forms. The exemplary embodiments are provided only to complete disclosure of the present invention and to fully provide a person having ordinary skill in the art to which the present invention pertains with the category of the invention, and the present invention will be defined only by the appended claims.

In Examples below, metformin hydrochloride (Metformin HCl) and phenformin hydrochloride (Phenformin HCl) were used among various pharmaceutically acceptable salt forms of metformin or phenformin as a biguanide-based compound. The form of these salts is not limited by Examples.

In the following Examples, inositol hexaphosphate (phytic acid) was used among several pharmaceutically acceptable salt forms of inositol hexaphosphate. The form of these salts is not limited by Examples.

In the following Examples, myo-inositol was used as an isomer of inositol. These isomers are not limited by Examples.

Cell Culture

Cells used in the test wereliver cancer (HepG2), lung cancer (A549), stomach cancer (AGS), pancreatic cancer (PANC-1), colon cancer (DLD-1), cervical cancer (HeLa), breast cancer (MDA-MB-231), prostate cancer (PC-3), ovarian cancer (SK-OV-3), bladder cancer (T24), glioblastoma (U-87 MG), osteosarcoma (Saos-2), and mouse-derived breast cancer (4T1) as tumor cells, and prostate (PZ-HPV-7), colon (CCD-18Co), and lung (MRCS) cell lines as non-tumor cells. All cell lines were purchased and used from the Korean Cell Line Bank or US American Type Culture Collection (ATCC) (Rockville, MD).

The cells were cultured and maintained in a 37° C. incubator (5% $CO_2$/95% air) using a cell culture solution obtained by adding 10% fetal bovine serum (FBS, Hyclone) and 1% penicillin/streptomycin (P/S, Hyclone) to a Roswell Park Memorial Institute 1640 medium (RPMI1640, Hyclone, Logan, UT, USA). When the cells were filled to about 80% of a culture dish, a single layer of the cells was washed with a phosphate-buffered saline (PBS, Hyclone) and subcultured with 0.25% trypsin-2.65 mM EDTA (Hyclone), and the medium was changed every two days.

Drug Used

Metformin HCl (hereinafter, referred to as MET), phenformin HCl (hereinafter, referred to as PHE), 2-deoxy-D-glucose (hereinafter, referred to as 2DG), inositol hexaphosphate (phytic acid, hereinafter, referred to as IP6), and myo-inositol (hereinafter, referred to as Ins) were purchased from Sigma (St. Louis, USA). In the present invention, all the drugs used in Table and the drawings summarizing the results obtained through a test were indicated as abbreviations.

REFERENCE EXAMPLE 1: CELL GROWTH INHIBITION ASSAY IN VITRO

Cytotoxicity of MET or PHE, 2DG and IP6 was confirmed by MTT assay [3-(4,5-dimethyl thiazolyl-2)-2,5-diphenyltetrazolium bromide assay]. After dispensing the cells (3 to $4 \times 10^5$ cells/well) into a 96-well culture plate and stabilizing for 12 hours or more, the medium of each well was removed and MET or PHE, 2DG, and IP6 for each cell were mixed for each concentration and treated with a medium without serum. For control cells, PBS was added in the medium. After incubation at 37° C. with $CO_2$ for 48 hours, the medium containing the control and the mixture was clearly removed and cultured at 37° C. for 4 hours with an MTT (Sigma Aldrich, St. Louis, MO, USA) reagent (0.5 mg/ml). Thereafter, the medium containing the MTT reagent was clearly removed and MTT formazan crystals formed by the living cells were left and dissolved at room temperature for 15 minutes or longer by adding DMSO (Sigma). Absorbance was measured at a wavelength of 560 nm using a micro plate reader (BioTek® Instruments, Inc., Winooski, VT, USA).

REFERENCE EXAMPLE 2: TEST METHOD FOR SINGLE FORMULATION AND COMPLEX FORMULATION

The cells (3 to $4 \times 10^5$ cells/well) were seeded in a 96-well plate and treated with each of MET or PHE, 2DG, and IP6 as a single formulation for each concentration to confirm a cell proliferation inhibition rate.

The complex formulation drug was treated with a concentration of a drug corresponding to IC50 of a complex formulation consisting of two or more compounds selected from the group consisting of MET or PHE, 2DG and IP6. All cell lines were cultured for 48 hours at the concentration of a single or complex formulation, and a growth inhibition effect was measured by MTT assay.

REFERENCE EXAMPLE 3: WESTERN BLOT ANALYSIS

In order to isolate proteins in cells, a total lysis buffer (50 mM Tris, 150 mM NaCl, 5 mM ethylenediaminetetraacetic acid (EDTA), 1 mM dithiothreitol (DTT), 0.5% nonidet P-40, 100 mM phenylmethylsulfonyl fluoride (PMSF), 20 mM aprotinin, 20 mM leupeptin, pH 8.0) was added and dissolved at 4° C. for 30 minutes, and then centrifuged (12,000 rpm, 10 minutes) to obtain a supernatant.

In addition, in order to isolate proteins in the cytoplasm/nucleus, a buffer solution A (10 mM Hepes (pH 7.9), 1.5 mM $MgCl_2$, 10 mM KCl, 0.5 mM DTT, 300 mM Saccharose, 0.1% NP-10, 0.5 mM PMSF) was added to the cells and dissolved at 4° C. for 5 minutes, and centrifuged (1,000 rpm, 1 minute) to isolate a pellet (nuclear protein). The isolated pellet was dissolved with a buffer solution B (20 mM Hepes (pH 7.9), 20% glycerol, 100 mM KCl, 100 mM $NaCl_2$, 0.2 mM EDTA, 0.5 mM DTT, 0.5 mM PMSF) for 15 minutes at 4° C. and centrifuged (10,000 rpm, 5 minutes) to isolate a protein in the nucleus.

The protein extracted by the above method was electrophoresed to a sodium dodecyl sulfate (SDS)-polyacrylamide gel and the protein was electrophoresed to a nitro-cellulose membrane (Whatman, GE Health Care Corp., Fairfield, CT, USA). In order to search for a specific protein, TBS-T containing 5% skim milk (GIBCO-BRL, Invitrogen Co., Grand Island, NY, USA) was reacted for 1 hour to block a non-specific protein, and then antibodies pAMPKa, ACCpS79, and b-actin (Santa Cruz Biotechnology Inc., Dallas, TX, USA) for the specific protein were diluted and reacted at 1:1000 in TBS-T containing 2.5% skim milk.

The reacted membrane was treated with a secondary antibody to a specific antibody and then photosensitized on an X-ray film using enhanced chemiluminescence (ECL, Amersham Life Science Corp. Arlington Heights, IL, USA) to analyze the expression of the specific protein.

REFERENCE EXAMPLE 4: TEST ANIMALS

Five-week-old, female specific pathogen free BALB/c nude mice were purchased and used from Orient Bio Co., Ltd. After quarantine and adaptation for one week, healthy animals without weight loss were selected and used in the test. The test animals were raised in a breeding environment set at a temperature of 23±3° C., a relative humidity of 50±10%, the ventilation number of 10 to 15 times/hour, lighting time of 12 hours (08:00 to 20:00), and illuminance of 150 to 300 Lux. During a pre-test period, the test animals were allowed to freely consume solid feed for the test animals (Cargill Agripurina Co., Ltd.) and drinking water.

REFERENCE EXAMPLE 5: TUMOR CELL TRANSPLANTATION AND TEST SUBSTANCE ADMINISTRATION

After an adaptation period for one week, in BALB/c nude mice, 4T1 cells ($1 \times 10^5$ cells/mouse), breast cancer cells, were injected to the left breast adipose tissues of the test animals, and then the tumor tissues were visually observed. When the tumor tissue size of the test animals was about 100 $mm^3$, the test animals were divided into 9 test groups based on a randomized block design. That is, the 9 test groups were classified into a control group, a MET group (MET 250 mg/kg), a 2DG group (2DG 500 mg/kg), an Ins group (Ins 500 mg/kg), a IP6 group (IP6 500 mg/kg), a MET+2DG group (MET 250 mg/kg+2DG 500 mg/kg), a MET+2DG+Ins group (MET 250 mg/kg+2DG 500 mg/kg+Ins 500 mg/kg), a MET+2DG+IP6 group (MET 250 mg/kg+2DG 500 mg/kg+IP6 500 mg/kg), a MET+2DG+IP6+Ins group (MET 250 mg/kg+2DG 500 mg/kg+IP6 250 mg/kg+Ins 250 mg/kg), and each test group used 10 test animals. The test substance was dissolved in distilled water and intraperitoneally administered at fixed time for 18 days.

REFERENCE EXAMPLE 6: MEASUREMENT OF BODY WEIGHT OF TEST ANIMAL AND TUMOR VOLUME

The body weight of the test animal during the test period was measured at a fixed time once a week from the test substance administration date. A tumor volume was measured by using a digital caliper every three days, the length and width of the tumor were measured, and the tumor volume was calculated by substituting the following Equation.

Tumor volume $(mm^3) = (width^2 \times length)/2$

REFERENCE EXAMPLE 7: MEASUREMENT OF TUMOR WEIGHT

After 14 days of administration of the test substance, the test animals were anesthetized using an anesthetic made by diluting tribromoethanol with tert-amyl alcohol and the blood was collected from the orbit. The blood was placed in a serum separate tube (Becton Dickinson) and left at room temperature for 30 minutes and centrifuged at 3,000 rpm for 20 minutes to isolate serum and the isolated serum was stored at −70° C. until analysis. After taking the blood from the test animals, the tumor was extracted and weighed. Tumors were weighed and some were fixed in 10% neutral buffered formalin (NBF, Sigma-Aldrich Co.) and embedded in paraffin to perform tissue immunostaining. The lung was fixed with a Bouin's solution (Sigma-Aldrich Co.), and the tumor nodule metastasized to the lung was observed and a lung metastasis rate was examined.

REFERENCE EXAMPLE 8: HEMATOXYLIN & EOSIN STAINING OF TUMOR TISSUE

A tumor tissue immobilized with 10% neutral buffered formalin was embedded in paraffin, and 5 mm of tissue sections were prepared from the embedded tissues. After paraffin removal, tissues were hydrated by sequentially lowering % of alcohol, starting with 100% alcohol to 0% ethanol ($H_2O$). H & E staining was performed according to a general method for histomorphological observation of tumor tissues, and histomorphological changes of the tumor tissues were observed by an optical microscopy (Carl Zeiss).

REFERENCE EXAMPLE 9: STATISTICAL PROCESSING

All analysis values were expressed as mean±SD. To compare a difference between a control group and a test substance-treated group, significance was verified by one-way ANOVA or two-way ANOVA testing using Tukey's multiple comparison post analysis using GraphPad Prism 6.0 software. It was determined that there was statistical significance only when p<0.05 or more.

Example 1. Cell Proliferation Inhibition Test of Single Formulation and Complex Formulation of MET (or PHE), 2DG and IP6

Cell proliferation inhibition effects of a single formulation and a complex formulation of MET (or PHE), 2DG and IP6 were compared using 12 types of cancer cells.

Example 1-1: Cell Survival Rate After Administering MET, 2DG and IP6 Alone and in Combination FIGS. 1 and 2 are diagrams of examining cell survival rate after administering MET, 2DG and IP6 alone or in combination based on human cancer cell lines such as liver cancer (HepG2), lung cancer (A549), gastric cancer (AGS), pancreatic cancer (PANC-1), colon cancer (DLD-1), cervical cancer (HeLa), breast cancer (MDA-MB-231), prostate cancer (PC-3), ovarian cancer (SK-OV-3), bladder cancer (T24), glioblastoma (U-87 MG), and osteosarcoma (Saos-2).

FIG. 1A shows cell survival rate in a liver cancer (HepG2) cell line treated alone and in combination with 4 mM of MET, 1 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 17.44±4.8, which was 2.6 times significantly lower than 45.40±4.2, the cell survival rate of a combination of MET+2DG (P<0.0001).

FIG. 1B shows cell survival rate in a lung cancer (A549) cell line treated alone and in combination with 4 mM of MET, 1 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 19.43±5.2, which was 2.5 times significantly lower 48.84±5.3, the cell survival rate of a combination of MET+2DG (P<0.0001).

FIG. 1C shows cell survival rate in a stomach cancer (AGS) cell line treated alone and in combination with 2 mM of MET, 0.7 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 15.20±4.2, which was 3.5 times significantly lower than 53.00±3.8, the cell survival rate of a combination of MET+2DG (P<0.0001).

FIG. 1D shows cell survival rate in a pancreatic cancer (PANC-1) cell line treated alone and in combination with 5 mM of MET, 0.7 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 25.27±5.2, which was 2.6 times significantly lower than 65.40±4.3, the cell survival rate of a combination of MET+2DG (P<0.0001).

FIG. 1E shows cell survival rate in a colon cancer (DLD-1) cell line treated alone and in combination with 5 mM of MET, 0.4 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 26.70±4.7, which was 2.4 times significantly lower than 65.40±4.6, the cell survival rate of a combination of MET+2DG (P<0.0001).

FIG. 1F shows cell survival rate in a cervical cancer (HeLa) cell line treated alone and in combination with 6 mM of MET, 0.5 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 24.67±3.6, which was 2.1 times significantly lower than 52.89±4.6, the cell survival rate of a combination of MET+2DG (P<0.0001).

FIG. 2A shows cell survival rate in a breast cancer (MDA-MB-231) cell line treated alone and in combination with 6 mM of MET, 1 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 26.37±5.3, which was 2.1 times significantly lower than 55.15±4.5, the cell survival rate of a combination of MET+2DG (P<0.0001).

FIG. 2B shows cell survival rate in a prostate cancer (PC-3) cell line treated alone and in combination with 5 mM of MET, 1 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 19.51±5.6, which was 3.4 times significantly lower than 66.70±4.6, the cell survival rate of a combination of MET+2DG (P<0.0001).

FIG. 2C shows cell survival rate in an ovarian cancer (SK-OV-3) cell line treated alone and in combination with 5 mM of MET, 0.5 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 22.80±5.2, which was 2.9 times significantly lower than 66.80±3.6, the cell survival rate of a combination of MET+2DG (P<0.0001).

FIG. 2D shows cell survival rate in a bladder cancer (T24) cell line treated alone and in combination with 4 mM of MET, 1 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 26.42±4.8, which was 2.4 times significantly lower than 63.30±4.2, the cell survival rate of a combination of MET+2DG (P<0.0001).

FIG. 2E shows cell survival rate in a glioblastoma (U-87 MG) cell line treated alone and in combination with 5 mM of MET, 0.4 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 20.80±5.7, which was 2.9 times significantly lower than 61.32±4.8, the cell survival rate of a combination of MET+2DG (P<0.0001).

FIG. 2F shows cell survival rate in an osteosarcoma (Saos-2) cell line treated alone and in combination with 5 mM of MET, 0.7 mM of 2DG, and 1 mM of IP6. A combination-treated formulation had significantly lower survival rate than single treatment including a control (P<0.0001). Compared between the combination-treated groups, the cell survival rate of a combination of MET+2DG+IP6 was 24.52±5.7, which was 2.6 times significantly lower than 64.33±4.9, the cell survival rate of a combination of MET+2DG (P<0.0001).

From these results, it was confirmed that the triple complex formulation of MET, 2DG and IP6 was a better cancer cell proliferation inhibitory effect than the single or double complex formulation.

Example 1-2: Cell Survival Rate After Administering PHE, 2DG and IP6 Alone and in Combination FIGS. 3 and 4 are diagrams of examining cell survival rate after administering PHE, 2DG and IP6 alone or in combination based on human cancer cell lines such as liver cancer (HepG2), lung cancer (A549), gastric cancer (AGS), pancreatic cancer (PANC-1), colon cancer (DLD-1), cervical cancer (HeLa), breast cancer (MDA-MB-231), prostate cancer (PC-3), ovarian cancer (SK-OV-3), bladder cancer (T24), glioblastoma (U-87 MG), and osteosarcoma (Saos-2).

FIG. 3A shows cell survival rate in a liver cancer (HepG2) cell line treated alone and in combination with 0.3 mM of PHE, 1 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 20.21±4.1, which was 2.5 times significantly lower than 49.55±4.8, the cell survival rate of a combination of PHE+2DG (P<0.0001).

FIG. 3B shows cell survival rate in a lung cancer (A549) cell line treated alone and in combination with 0.3 mM of PHE, 1 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 22.41±5.2, which was 2.4 times significantly lower than 54.77±5.8, the cell survival rate of a combination of PHE+2DG (P<0.0001).

FIG. 3C shows cell survival rate in a stomach cancer (AGS) cell line treated alone and in combination with 0.3 mM of PHE, 0.7 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 17.38±3.8, which was 2.9 times significantly lower than 50.45±3.9, the cell survival rate of a combination of PHE+2DG (P<0.0001).

FIG. 3D shows cell survival rate in a pancreatic cancer (PANC-1) cell line treated alone and in combination with 0.2 mM of PHE, 0.7 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 25.27±5.2, which was 2.6 times significantly lower than 65.40±4.3, the cell survival rate of a combination of PHE+2DG (P<0.0001).

FIG. 3E shows cell survival rate in a colon cancer (DLD-1) cell line treated alone and in combination with 0.3 mM of PHE, 0.4 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 22.21±4.8, which was 2.7 times significantly lower than 60.98±4.7, the cell survival rate of a combination of PHE+2DG (P<0.0001).

FIG. 3F shows cell survival rate in a cervical cancer (HeLa) cell line treated alone and in combination with 0.2 mM of PHE, 0.5 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 25.65±3.9, which was 2.1 times significantly lower than 54.67±4.6, the cell survival rate of a combination of PHE+2DG (P<0.0001).

FIG. 4A shows cell survival rate in a breast cancer (MDA-MB-231) cell line treated alone and in combination with 0.2 mM of PHE, 1 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 20.76±4.2, which was 2.3 times significantly lower than 48.54±4.5, the cell survival rate of a combination of PHE+2DG (P<0.0001).

FIG. 4B shows cell survival rate in a prostate cancer (PC-3) cell line treated alone and in combination with 0.3 mM of PHE, 1 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 20.77±4.3, which was 2.9 times significantly lower than 59.66±4.6, the cell survival rate of a combination of PHE+2DG (P<0.0001).

FIG. 4C shows cell survival rate in an ovarian cancer (SK-OV-3) cell line treated alone and in combination with 0.4 mM of PHE, 0.5 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 20.44±4.2, which was 3.0 times significantly lower than 60.54±5.1, the cell survival rate of a combination of PHE+2DG (P<0.0001).

FIG. 4D shows cell survival rate in a bladder cancer (T24) cell line treated alone and in combination with 0.4 mM of PHE, 1 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 21.45±4.2, which was 2.7 times significantly lower than 58.70±4.5, the cell survival rate of a combination of PHE+2DG (P<0.0001).

FIG. 4E shows cell survival rate in a glioblastoma (U-87 MG) cell line treated alone and in combination with 0.2 mM of PHE, 0.4 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 15.76±4.2, which was 3.4 times significantly lower than 54.32±4.8, the cell survival rate of a combination of PHE+2DG (P<0.0001).

FIG. 4F shows cell survival rate in an osteosarcoma (Saos-2) cell line treated alone and in combination with 0.2 mM of PHE, 0.7 mM of 2DG, and 1 mM of IP6. A combination-treated formulation had significantly lower survival rate than single treatment including a control (P<0.0001). Compared between the combination-treated groups, the cell survival rate of a combination of PHE+2DG+IP6 was 22.76±4.2, which was 2.7 times significantly lower than 61.93±4.7, the cell survival rate of a combination of PHE+2DG (P<0.0001).

From these results, it was confirmed that the triple-complex formulation of PHE, 2DG and IP6 was a better cancer cell proliferation inhibitory effect than the single or double-complex formulation.

Example 2: Effect of Complex Formulation of MET, 2DG and IP6 on Normal Cells

FIG. 5 is a diagram of examining cytotoxicity by MTT assay after 48 hours after treating a three-combined formulation to prostate cancer (PC-3), colon cancer (DLD-1), and lung cancer (A549) cell lines as tumor cells and prostate (PZ-HPV-7), colon (CCD-18Co) and lung (MRCS) cell lines as non-tumor cells in order to look into an effect of a complex formulation of MET, 2DG and IP6 on normal cells.

As a result in PC-3 and PZ-HPV-7 cell lines treated with a complex formulation of 5 mM of MET, 1 mM of 2DG, and 1 mM of IP6, the cell survival rate was significantly reduced in a PC-3 cell line as tumor cells, while a PZ-HPV-7 cell line as non-tumor cells did not affect cell survival rate (P<0.0001).

As a result in DLD-1 and CCD-18Co cell lines treated with a complex formulation of 5 mM of MET, 0.4 mM of 2DG, and 1 mM of IP6, the cell survival was significantly reduced in a DLD-1 cell line as tumor cells, while a CCD-18Co cell line as non-tumor cells did not affect cell survival rate (P<0.0001).

As a result in A549 and MRCS cell lines treated with a complex formulation of 4 mM of MET, 1 mM of 2DG, and 1 mM of IP6, the cell survival rate was significantly reduced in a A549 cell line as tumor cells, while a MRCS cell line as non-tumor cells did not affect cell survival rate (P<0.0001).

Apoptosis for each non-tumor cells of the three-combined formulation showed a different pattern from tumor cells and the three-combined formulation was confirmed to be a safe drug in vivo.

Example 3: Cell Survival Rate and Protein Expression of 4T1 Cells by Single and Complex Formulations of MET. 2DG and IP6

The metabolism of living cells uses ATP and ADP as energy sources and produces AMPs. AMP-activated protein kinase (AMPK) is a serine/threonine kinase known as a regulator of lipid and glucose metabolism and plays an important regulatory role in ophthalmic diabetes. The AMPK is activated by AMP to inhibit ATP use, wherein AMP increases when cellular energy is consumed, and plays a key role in maintaining homeostasis by inducing catabolism. AMPK activation inhibits the proliferation of cancer cells and inhibits acetyl CoA carboxylase (ACC), an enzyme that induces fatty acid synthesis in terms of fat metabolism.

FIG. 6A shows cell survival rate in a mouse-derived breast cancer (4T1) cell line treated alone and in combination with 5 mM of MET, 2 mM of 2DG, and 1 mM of IP6. A combination-treated formulation had significantly lower survival rate than single treatment including a control (P<0.0001). In comparison between the combination-treated groups, the cell survival rate of a (MET+2DG+IP6) group was 23.04±4.0, which was reduced 2.2 times significantly lower than 50.03±4.0, the cell survival rate of a (MET+2DG) group (P<0.0001).

In FIGS. 6B and 6C, AMPK is significantly activated (P<0.0001) and phosphorylation of ACC is reduced (P<0.05) in the (MET+2DG+IP6) group compared with the (MET+2DG) group.

Example 4. ATP Synthesis Inhibition of Single and Complex Dormulations of MET, 2DG and IP6 for 4T1 Cells ATP (adenosine triphosphate) is an energy source for living organisms, and when intracellular ATP synthesis is inhibited, energy metabolism activity is reduced. An ATP synthesis inhibitory effect of MET, 2DG, and IP6 was confirmed in a mouse-derived breast cancer cell line 4T1 of Example 3.

Each cell ($10^3$-$10^4$ cells) of 4T1 was incubated for 24 hours in a 60 mm culture dish, and treated alone and in combination with 4 mM of MET, 1 mM of 2DG, and 1 mM of IP6, and further incubated for 48 hours. Thereafter, cells were harvested and counted and diluted in 100 ml of an RPMI culture solution containing 10 volume % FBS, and was transferred to each well of a 96-well plate. 100 ml of an assay buffer (rL/L reagent+reconstitution buffer) of a Promega ATP assay kit (G7572, Promega, Durham, NC, USA) was added to the wells containing the cells, and the emission of fluorescence was measured at 560 nm. The results were shown in FIG. 7.

As shown in FIG. 7, test results showed that ATP synthesis was inhibited in the combination treatment rather than single treatment in single and combination treatments in a 4T1 cell line used in the test (P<0.0001). The MET+2DG+IP6 group was found to significantly inhibit ATP synthesis as compared with the MET+2DG group (P<0.05). As a result, it can be seen that the complex formulation of the MET+2DG+IP6 group reduces the energy level most effectively in cancer cells.

Example 5. Effect of Single and Complex Formulations of MET, 2DG, and IP6 on Tumor Volume Change When the size of a tumor tissue was about 100 $mm^3$, test groups were classified and test substance administration was started, and the tumor volume was measured at 3 days intervals from the start date of the test substance administration. As a result of the test, as shown in FIG. 8, the volumes of tumors of single and combination-treated groups were reduced compared to a control group from the day 3 of the test substance administration. On day 18 of the test substance administration, compared with a control group having a tumor volume of 1486.8±67.0 $mm^3$, as single-administered groups, as 1400.5±58.6 $mm^3$ in an MET group, 1350.3±55.2 $mm^3$ in a 2DG group, 1108.5±66.3 $mm^3$ in an IP6 group, and 1190.1±67.3 $mm^3$ in an Ins group, tumor volumes were slightly reduced, but there was no significant difference. However, 820.1±67.0 mm³ of the MET+2DG group showed a significant difference higher than the control group and the single-administered group (P<0.0001). The tumor volume in the complex formulation, 515.02±54.9 mm³ in the MET+2DG+IP6 group and 350.03±33.0 mm³ in the MET+2DG+IP6+Ins group, showed a significant difference higher than MET+2DG group (P<0.0001). The MET+2DG+IP6 group and the MET+2DG+Ins group showed a significant difference in comparison with the MET+2DG+IP6 +Ins group (P<0.05), and the MET+2DG+IP6+Ins group had the highest reduction and showed a high tumor growth inhibitory effect (FIG. 8).

Example 6. Effect of Single and Complex Formulations of MET, 2DG, and IP6 on Tumor Weight On day 19 of the administration of a test substance, tumors were extracted by sacrificing test animals and the weights of the tumors were measured and shown in FIG. 9. The tumor weight of a control group was 1.244±0.22 g, the tumor weights were 1.134±0.15 gin an MET group, 1.092±0.18 g in a 2DG group, 0.874±0.18 gin an IP6 group, and 0.904±0.20 g in an Ins group, but the complex formulation significantly decreased tumor weight as 0.621±0.14 g in an MET+2DG group and 0.599±0.12 gin an IP6+Ins group (P<0.0001). In addition, 0.342±0.11 g of a MET+2DG+IP6 group and 0.203±0.06 g of a MET+2DG+IP6+Ins group showed a significant difference higher than a control group and single administration (P<0.0001) and showed a significant difference from the MET+2DG group as the double-complex formulation (P<0.01). There was also a significant difference from the MET+2DG+IP6 group and the MET+2DG+IP6+Ins group (P<0.05), and overall, the MET+2DG+IP6+Ins group showed the largest reduction in tumor size (FIG. 9).

Example 7. Effect on Body Weight of Test Animals

The body weights of animals were measured once every six days during a test period. There was no significant difference in weight loss between the singe and combined-treated groups compared to the control group on day 6 of administration of the test substance. At the end of the test, on day 18 of administration of the test substance, there was no significant difference in weight loss as 22.90±0.41 g in the MET+2DG group, 22.90±0.47 g in the MET+2DG+IP6 group, and 22.90±0.50 g in the MET+2DG+IP6+Ins group compared to 23.34±0.52 g in the control group (FIG. 10).

Example 8. Effect of Single and Complex Formulations of MET, 2DG, and IP6 on Incidence of Lung Metastasis It was observed that cancer cells were metastasized to the lung in a tumor animal model. In order to examine an effect of a test substance on metastasis, the incidence of lung metastasis was examined and shown in FIG. 11. The incidence of lung metastasis was 100% (10 of 10) in the control, MET groups, and 2DG groups, but the incidence of lung metastasis was reduced to 90% (9 of 10) in the IP6 group, 90% (9 of 10) in the Ins group, 80% (8 of 10) in the MET+2DG group, 80% (8 of 10) of the IP6+Ins group, 30% (3 of 10) of the MET+2DG+IP6 group, 30% (3 of 10) of the MET+2DG+Ins group, and 20% (2 of 10) of the MET+2DG+IP6+Ins group. The incidence of lung metastasis of the MET+2DG+IP6+Ins group showed the highest inhibition among each test group (FIG. 11).

Example 9. Effect on Histomorphological Change of Tumor Tissue

FIG. 12 shows results of microscopic observation after H & E staining to examine histomorphological changes of tumor tissues by the test substance. The outer periphery of the control tumor tissue was densely composed of 4T1 cells, and coagulative necrosis was observed at the center. The tumor tissues in the MET+2DG group and the IP6+Ins group were increased in the coagulation necrosis region of the center compared to the control group, and in the case of the MET+2DG+IP6 group, the MET+2DG+Ins group, and the MET+2DG+IP6+Ins group, a ratio of normal 4T1 cells was significantly reduced (FIG. 12).

The invention claimed is:

1. A method for treating cancer comprising administering a therapeutically effective amount of:
   a biguanide-based compound or a pharmaceutically acceptable salt thereof;
   2-deoxy-D-glucose; and
   inositol hexaphosphate or a pharmaceutically acceptable salt thereof, inositol, or a mixture thereof
   to a subject in need thereof,
   wherein the biguanide-based compound is metformin or a pharmaceutically acceptable salt thereof, wherein a weight ratio of metformin or a pharmaceutically acceptable salt thereof: 2-deoxy-D-glucose: inositol hexaphosphate or a pharmaceutically acceptable salt thereof, or inositol is in a range of 1:0.2:0.5 to 1:5: 20, or
   wherein the biguanide-based compound is phenformin and wherein a weight ratio of phenformin or a pharmaceutically acceptable salt thereof: 2-deoxy-D-glucose: inositol hexaphosphate or a pharmaceutically acceptable salt thereof, or inositol is in a range of 1:1: 1 to 1:50: 200, or
   wherein the biguanide-based compound is metformin and administering comprise administering a therapeutic effective amount of inositol hexaphosphate and inositol, and wherein a weight ratio of metformin or a pharmaceutically acceptable salt thereof: 2-deoxy-D-glucose: inositol hexaphosphate or a pharmaceutically acceptable salt thereof: inositol is in a range of 1:0.2: 0.5:0.5 to 1:5: 20:20, or
   wherein the biguanide-based compound is phenformin and administering comprise administering a therapeutic effective amount of inositol hexaphosphate and inositol, and wherein a weight ratio of phenformin or a pharmaceutically acceptable salt thereof: 2-deoxy-D-glucose: inositol hexaphosphate or a pharmaceutically acceptable salt thereof: inositol is in a range of 1:1: 1:1 to 1:50: 200:200.

2. The method of claim 1, wherein the inositol compound comprises at least one isomer of D-chiro-inositol, L-chiro-inositol, myo-inositol, and scyllo-inositol.

3. The method of claim 1, wherein the cancer comprises at least one of liver cancer, lung cancer, stomach cancer, pancreatic cancer, colon cancer, cervical cancer, breast cancer, prostate cancer, ovarian cancer, brain cancer, osteosarcoma, and bladder cancer.

4. A composition comprising a combination of:
a biguanide-based compound or a pharmaceutically acceptable salt thereof;
2-deoxy-D-glucose; and
inositol hexaphosphate or a pharmaceutically acceptable salt thereof, inositol, or a mixture thereof,
wherein the biguanide-based compound is metformin and wherein a weight ratio of metformin or a pharmaceutically acceptable salt thereof: 2-deoxy-D-glucose: inositol hexaphosphate or a pharmaceutically acceptable salt thereof, or inositol is in a range of 1: 0.2:0.5 to 1:5: 20, or
wherein the biguanide-based compound is phenformin and wherein a weight ratio of phenformin or a pharmaceutically acceptable salt thereof: 2-deoxy-D-glucose: inositol hexaphosphate or a pharmaceutically acceptable salt thereof, or inositol is in a range of 1:1: 1 to 1:50: 200, or
wherein the biguanide-based compound is metformin and administering comprise administering a therapeutic effective amount of inositol hexaphosphate and inositol, and wherein a weight ratio of metformin or a pharmaceutically acceptable salt thereof: 2-deoxy-D-glucose: inositol hexaphosphate or a pharmaceutically acceptable salt thereof: inositol is in a range of 1:0.2: 0.5:0.5 to 1:5: 20:20, or
wherein the biguanide-based compound is phenformin and administering comprise administering a therapeutic effective amount of inositol hexaphosphate and inositol, and wherein a weight ratio of phenformin or a pharmaceutically acceptable salt thereof: 2-deoxy-D-glucose: inositol hexaphosphate or a pharmaceutically acceptable salt thereof: inositol is in a range of 1:1: 1:1 to 1:50: 200:200.

5. A composition comprising:
a biguanide-based compound or a pharmaceutically acceptable salt thereof;
2-deoxy-D-glucose;
inositol hexaphosphate or a pharmaceutically acceptable salt thereof, inositol, or a mixture thereof; and
a pharmaceutically acceptable carrier,
wherein the biguanide-based compound is metformin and wherein a weight ratio of metformin or a pharmaceutically acceptable salt thereof: 2-deoxy-D-glucose: inositol hexaphosphate or a pharmaceutically acceptable salt thereof, or inositol is in a range of 1: 0.2:0.5 to 1:5: 20, or
wherein the biguanide-based compound is phenformin and wherein a weight ratio of phenformin or a pharmaceutically acceptable salt thereof: 2-deoxy-D-glucose: inositol hexaphosphate or a pharmaceutically acceptable salt thereof, or inositol is in a range of 1:1: 1 to 1:50: 200, or
wherein the biguanide-based compound is metformin and administering comprise administering a therapeutic effective amount of inositol hexaphosphate and inositol, and wherein a weight ratio of metformin or a pharmaceutically acceptable salt thereof: 2-deoxy-D-glucose: inositol hexaphosphate or a pharmaceutically acceptable salt thereof: inositol is in a range of 1:0.2: 0.5:0.5 to 1:5: 20:20, or
wherein the biguanide-based compound is phenformin and administering comprise administering a therapeutic effective amount of inositol hexaphosphate and inositol, and wherein a weight ratio of phenformin or a pharmaceutically acceptable salt thereof: 2-deoxy-D-glucose: inositol hexaphosphate or a pharmaceutically acceptable salt thereof: inositol is in a range of 1:1: 1:1 to 1:50: 200:20 .

* * * * *

UNITED STATES PATENT AND TRADEMARK OFFICE
CERTIFICATE OF CORRECTION

| | | |
|---|---|---|
| PATENT NO. | : 12,370,155 B2 | Page 1 of 1 |
| APPLICATION NO. | : 17/293390 | |
| DATED | : July 29, 2025 | |
| INVENTOR(S) | : Man-Chul Suh et al. | |

It is certified that error appears in the above-identified patent and that said Letters Patent is hereby corrected as shown below:

On the Title Page

At item (57), Line 14, "thus be" should be -- thus may be --.

In the Claims

At Column 26, Line 34, "1:50: 200:20 ." should be -- 1:50: 200:200. --.

Signed and Sealed this
Eighteenth Day of November, 2025

John A. Squires
*Director of the United States Patent and Trademark Office*